(12) United States Patent
Rouge et al.

(10) Patent No.: US 11,937,861 B2
(45) Date of Patent: *Mar. 26, 2024

(54) DEVICES AND METHODS FOR BENDING OR CUTTING IMPLANTS

(71) Applicant: Medos International Sarl, Le Locle (CH)

(72) Inventors: Renaud Rouge, Le Locle (CH); Henri Defossez, Neuchatel (CH); Thibault Chandanson, Villers le lac (FR); Joseph Caulfield, Galway (IE); Daniel Lyness, Le Locle (CH); Zoher Bootwala, Foxboro, MA (US); Michael O'Neil, West Barnstable, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 449 days.

This patent is subject to a terminal disclaimer.

(21) Appl. No.: 17/321,397

(22) Filed: May 14, 2021

(65) Prior Publication Data
US 2021/0275239 A1  Sep. 9, 2021

Related U.S. Application Data

(60) Continuation of application No. 16/100,958, filed on Aug. 10, 2018, now Pat. No. 11,033,314, which is a
(Continued)

(51) Int. Cl.
*A61B 17/88* (2006.01)
*B21D 7/00* (2006.01)
*B21D 11/00* (2006.01)

(52) U.S. Cl.
CPC ............ *A61B 17/8863* (2013.01); *B21D 7/00* (2013.01); *B21D 11/00* (2013.01)

(58) Field of Classification Search
CPC .................................................. A61B 17/0682
See application file for complete search history.

(56) References Cited

U.S. PATENT DOCUMENTS

| 401,308 | A | 4/1889 | Selleck |
|---|---|---|---|
| 1,636,786 | A | 7/1927 | Rolley |

(Continued)

FOREIGN PATENT DOCUMENTS

| GB | 461399 A | 2/1937 |
|---|---|---|
| WO | 2014088801 A1 | 6/2014 |
| WO | 2014143762 A2 | 9/2014 |

OTHER PUBLICATIONS

U.S. Appl. No. 14/723,263, filed May 27, 2015, Devices and Methods for Bending or Cutting Implants.
(Continued)

*Primary Examiner* — Andrew Yang
(74) *Attorney, Agent, or Firm* — Barnes & Thornburg LLP

(57) ABSTRACT

Devices and methods for bending or cutting implants are disclosed herein. In some embodiments, an instrument can include a rotatable drive shaft that urges first and second portions of a modular bending or cutting template toward one another to bend or cut an implant disposed between the template portions. A linkage assembly can be included to provide a mechanical advantage in urging the template portions toward one another. In some embodiments, an instrument can include a rotatable drive shaft that, depending on direction of rotation, pushes or pulls a first modular template portion with respect to a second modular template portion to bend an implant disposed between the template portions in one direction or another direction. In some embodiments, an instrument can include a worm drive that rotates a cutting wheel with respect to a cutting plate to cut
(Continued)

an implant inserted through openings formed in the cutting wheel and the cutting plate.

20 Claims, 11 Drawing Sheets

Related U.S. Application Data division of application No. 14/723,263, filed on May 27, 2015, now Pat. No. 10,076,376, and a division of application No. 14/723,266, filed on May 27, 2015, now Pat. No. 10,070,909.

(56) References Cited

U.S. PATENT DOCUMENTS

| | | |
|---|---|---|
| 1,775,761 A | 9/1930 | Harvey et al. |
| 2,762,415 A | 9/1956 | Franck |
| 2,818,786 A | 1/1958 | Hammer |
| 2,986,195 A | 5/1961 | Landis |
| 3,260,091 A | 7/1966 | Ralph, Jr. |
| 3,575,032 A | 4/1971 | Zahuranec et al. |
| 3,680,347 A | 8/1972 | Schenck et al. |
| 4,888,971 A | 12/1989 | Schwarze |
| 5,144,829 A | 9/1992 | Fabro et al. |
| 5,243,760 A | 9/1993 | May, Jr. |
| 6,644,087 B1 | 11/2003 | Ralph et al. |
| 6,755,064 B2 | 6/2004 | Butscher et al. |
| 7,882,721 B2 | 2/2011 | Gombas |
| 8,177,843 B2 | 5/2012 | Schalliol |
| 8,235,998 B2 | 8/2012 | Miller et al. |
| 8,266,940 B2 | 9/2012 | Riemeier et al. |
| 8,298,242 B2 | 10/2012 | Justis et al. |
| 8,333,097 B1 | 12/2012 | Frear |
| 8,607,603 B2 | 12/2013 | Justis et al. |
| 8,935,974 B2 | 1/2015 | Crainich et al. |
| 8,991,229 B1 | 3/2015 | Cheng |
| 10,070,909 B2 | 9/2018 | Rouge et al. |
| 10,076,376 B2 | 9/2018 | Bootwala et al. |
| 10,194,957 B2 | 2/2019 | Rouge et al. |
| 11,033,314 B2 | 6/2021 | Rouge et al. |
| 2003/0055435 A1 | 3/2003 | Barrick |
| 2004/0144149 A1* | 7/2004 | Strippgen ............. B21D 11/06 72/173 |
| 2005/0262911 A1 | 12/2005 | Dankowicz et al. |
| 2006/0037198 A1 | 2/2006 | Sullivan |
| 2010/0111631 A1 | 5/2010 | Trieu et al. |
| 2012/0186411 A1 | 7/2012 | Lodahi et al. |
| 2012/0247173 A1 | 10/2012 | Paris et al. |
| 2014/0000335 A1 | 1/2014 | Fries et al. |
| 2014/0066994 A1 | 3/2014 | Dominik et al. |
| 2014/0311203 A1 | 10/2014 | Crawford et al. |
| 2016/0074918 A1 | 3/2016 | Latoria |
| 2016/0082493 A1 | 3/2016 | Neal et al. |
| 2016/0089195 A1 | 3/2016 | Cordaro et al. |
| 2016/0346026 A1 | 12/2016 | Bootwala et al. |
| 2016/0346027 A1 | 12/2016 | Rouge et al. |
| 2017/0325854 A1 | 11/2017 | Rouge et al. |
| 2019/0038332 A1 | 2/2019 | Rouge et al. |
| 2019/0167317 A1 | 6/2019 | Rouge et al. |
| 2022/0330990 A1 | 10/2022 | Rouge et al. |

OTHER PUBLICATIONS

U.S. Appl. No. 14/723,266, filed May 27, 2015, Devices and Methods for Bending or Cutting Implants.
U.S. Appl. No. 15/154,717, filed May 13, 2016, Devices and Methods for Bending or Cutting Implants.
U.S. Appl. No. 16/100,958, filed Aug. 10, 2018, Devices and Methods for Bending or Cutting Implants.
U.S. Appl. No. 16/266,849, filed Feb. 4, 2019, Devices and Methods for Bending or Cutting Implants.
U.S. Appl. No. 17/855,718, filed Jun. 30, 2022, Devices and Methods for Bending or Cutting Implants.
[No Author Listed] Expedium® 5.5 Titanium Spine System, Product Catalog; 2013 DePuy Synthes Spine (34 pages).

* cited by examiner

DEVICES AND METHODS FOR BENDING OR CUTTING IMPLANTS

CROSS-REFERENCE TO RELATED APPLICATIONS

This application is a continuation of U.S. patent application Ser. No. 16/100,958, filed Aug. 10, 2018. U.S. patent application Ser. No. 16/100,958 is a divisional of U.S. patent application Ser. No. 14/723,266, filed May 27, 2015 (now issued as U.S. Pat. No. 10,070,909). U.S. patent application Ser. No. 16/100,958 is also a divisional of U.S. patent application Ser. No. 14/723,263, filed May 27, 2015 (now issued as U.S. Pat. No. 10,076,376). The entire contents of these applications are incorporated by reference herein.

FIELD

Devices and methods for bending or cutting implants are disclosed herein.

BACKGROUND

There is often a need to bend or cut an implant during a surgical procedure or in preparation for a surgical procedure. For example, spinal rods are typically cut to a desired length and bent to a desired shape before being implanted in a patient. Often times, several bends are necessary to form a compound or complex bend along the length of a large implant. Forming the final shape can be an iterative process in which the implant is bent, checked for fit, and then bent again until the desired shape is achieved.

Existing solutions for bending or cutting implants have numerous shortcomings. The bending and cutting tools used today are very large and are not capable of bending an implant that is at least partially implanted in the patient. Instead, these tools are typically used at a back table in the operating room, remote from the patient and the surgical site. As a result, the surgeon usually needs to make several trips back and forth between the patient and the back table to make adjustments until the final implant shape is achieved. Existing tools also require significant input force from the surgeon, which increases surgeon fatigue. These tools also lack precision, which increases the number of adjustments that must be made to the implant. In some cases, repeated bending and adjustment of the implant can reduce the implant strength.

There is a continual need for improved cutting and/or bending devices and related methods.

SUMMARY

Devices and methods for bending or cutting implants are disclosed herein. In some embodiments, an instrument can include a rotatable drive shaft that urges first and second portions of a modular bending or cutting template toward one another to bend or cut an implant disposed between the template portions. A linkage assembly can be included to provide a mechanical advantage in urging the template portions toward one another. In some embodiments, an instrument can include a rotatable drive shaft that, depending on direction of rotation, pushes or pulls a first modular template portion with respect to a second modular template portion to bend an implant disposed between the template portions in one direction or another direction. In some embodiments, an instrument can include a worm drive that rotates a cutting wheel with respect to a cutting plate to cut an implant inserted through openings formed in the cutting wheel and the cutting plate.

In some embodiments, an instrument for cutting or bending an implant includes a cutting or bending template having a first portion and a second portion; a body to which the first portion of the template is coupled; a pusher to which the second portion of the template is coupled; and a drive shaft rotatably mounted in the body and the pusher such that rotation of the drive shaft is effective to urge the pusher towards the body along a longitudinal axis of the drive shaft to bend or cut an implant disposed between the first and second portions of the template.

The instrument can include an adapter in which a proximal end of the drive shaft is rotatably mounted. The adapter can include anti-rotation features configured to non-rotatably couple the adapter to a driver tool. The instrument can include a linkage assembly configured to provide a mechanical advantage in urging the pusher towards the body. The linkage assembly can include first and second arms coupled to the body and to the adapter by respective first and second scissor linkages. The first and second arms can be coupled to the pusher by respective first and second distal links. Rotation of the drive shaft can be effective to pull the first and second arms inwards towards the drive shaft. Inward movement of the first and second arms can cause the first and second distal links to pivot and urge the pusher proximally. The drive shaft can include a threaded distal portion mounted in a threaded bore formed in the pusher and a threaded intermediate portion mounted in a threaded bore of the body. The threaded distal portion of the drive shaft and the threaded intermediate portion of the drive shaft can be threaded in opposite directions. The first portion of the template can include at least one bending block configured to engage an implant along an outside of a bend to be formed in the implant and the second portion of the template can include at least one bending block configured to engage an implant along an inside of a bend to be formed in the implant. The first portion of the template can include a bending block having a recess formed therein that defines a negative of an outside portion of a bend to be formed in an implant and the second portion of the template can include a bending block having a recess formed therein that defines a negative of an inside portion of a bend to be formed in an implant. The first portion of the template can include a cutting block having a lateral bore formed therein configured to receive an implant therethrough and the second portion of the template can include a cutting blade configured to intersect the lateral bore to sever an implant disposed therein when the second portion is urged towards the first portion. The cutting block can be configured to retain cut portions of an implant therein after the implant is severed by the cutting blade. Rotation of the drive shaft in a first direction can urge the pusher towards the body to bend an implant proximally and rotation of the drive shaft in a second, opposite direction can urge the pusher away from the body to bend an implant distally. The first portion of the template can include proximal and distal bending blocks coupled to each of first and second arms that extend distally from the body. The second portion of the template can include proximal and distal bending blocks coupled to the pusher.

In some embodiments, an instrument for cutting or bending an implant includes a body having first and second arms extending distally therefrom, each of the first and second arms having proximal and distal template portions coupled thereto; a pusher having proximal and distal template portions coupled thereto; and a drive shaft rotatably mounted in the body and the pusher such that: rotation of the drive shaft in a first direction is effective to urge the pusher towards the body along a longitudinal axis of the drive shaft to bend or cut an implant disposed between the distal template portion of the pusher and the proximal template portions of the first and second arms; and rotation of the drive shaft in a second opposite direction is effective to urge the pusher away from the body along a longitudinal axis of the drive shaft to bend or cut an implant disposed between the proximal template portion of the pusher and the distal template portions of the first and second arms.

The drive shaft can be threadably mounted within a threaded bore formed in the pusher. The first and second arms can be pivotally coupled to the body. The first and second arms can each include a telescoping portion. The instrument can include a guide rail extending parallel to the drive shaft configured to prevent the pusher from rotating relative to the body. The guide rail can be formed in one of the first and second arms. The guide rail can include a cylindrical rod that extends through an opening formed in the pusher. The guide rail can include a track along which the pusher slides. The instrument can include a first template comprising the template portions of the body and the template portions of the pusher and a second template, wherein the second template differs in at least one of size and shape from the first template. The first and second templates can be interchangeably coupled to the instrument. The first and second templates can be simultaneously coupled to the instrument.

In some embodiments, a method of bending or cutting an implant using an instrument includes positioning an implant between first and second portions of a bending or cutting template of the instrument; and rotating a drive shaft of the instrument to urge the first and second portions of the template toward one another along a longitudinal axis of the drive shaft to bend or cut the implant.

The first portion of the template can be coupled to a body of the instrument and the second portion of the template can be coupled to a pusher of the instrument. Rotating the drive shaft can actuate a scissor linkage to provide a mechanical advantage in urging the pusher towards the body. Rotating the drive shaft can include selecting between rotating the drive shaft in a first direction to bend the implant proximally and rotating the drive shaft in a second, opposite direction to bend the implant distally. Rotating the drive shaft can pull first and second arms of the instrument inwards towards the drive shaft. The implant can be at least partially implanted in a patient during said positioning and said rotating. The method can include adjusting a distance between components of the first portion of the template to adjust an angle of a bend formed in the implant.

In some embodiments, an instrument for cutting an implant includes a housing having a drive shaft rotatably mounted therein, at least a portion of the drive shaft comprising a worm screw; a cutting wheel having at least one opening formed therein through which an implant can be received and a worm gear configured to engage the worm screw of the drive shaft such that rotation of the drive shaft is effective to rotate the cutting wheel; and a cutting plate having at least one opening formed therein through which an implant can be received; wherein rotation of the drive shaft is effective to rotate the cutting wheel relative to the cutting plate to cut an implant disposed through the at least one opening of the cutting wheel and the at least one opening of the cutting plate.

The at least one opening formed in the cutting wheel can include an elongated bean-shaped opening. The at least one opening formed in the cutting wheel can include a plurality of rings of openings, each ring of openings having a radial dimension that differs from the other rings of openings. The at least one opening formed in the cutting plate can include a plurality of circular openings, each circular opening having a different diameter. The cutting plate can be formed integrally with the housing. The worm screw and the worm gear can provide a mechanical advantage in rotating the cutting wheel with respect to the cutting plate. The drive shaft can be mounted in the housing by proximal and distal race bearings.

In some embodiments, a method of cutting an implant includes positioning an implant with respect to an instrument such that the implant simultaneously extends through an opening formed in a cutting wheel of the instrument and through an opening formed in a cutting plate of the instrument; and rotating a drive shaft of the instrument to rotate the cutting wheel with respect to the cutting plate and thereby apply a shear force to the implant to cut the implant.

Rotating the drive shaft can rotate a worm screw of the drive shaft that engages a worm gear of the cutting wheel to rotate the cutting wheel. Positioning the implant can include selecting the opening in the cutting wheel in which the implant is positioned from among a plurality of openings formed in the cutting wheel. The opening in the cutting wheel can be selected based on a size of the implant. The opening in the cutting wheel can be selected based on alignment of the opening with the opening formed in the cutting plate. Rotating the drive shaft can include coupling a housing in which the drive shaft is disposed to a non-rotating component of a power driver, coupling the drive shaft to a rotating component of the power driver, and actuating the power driver to rotate the drive shaft relative to the housing. The drive shaft can be rotated about a longitudinal axis of the drive shaft and the cutting wheel can be rotated about an axis that extends perpendicular to a plane in which the longitudinal axis of the drive shaft lies.

The present invention further provides devices and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1:
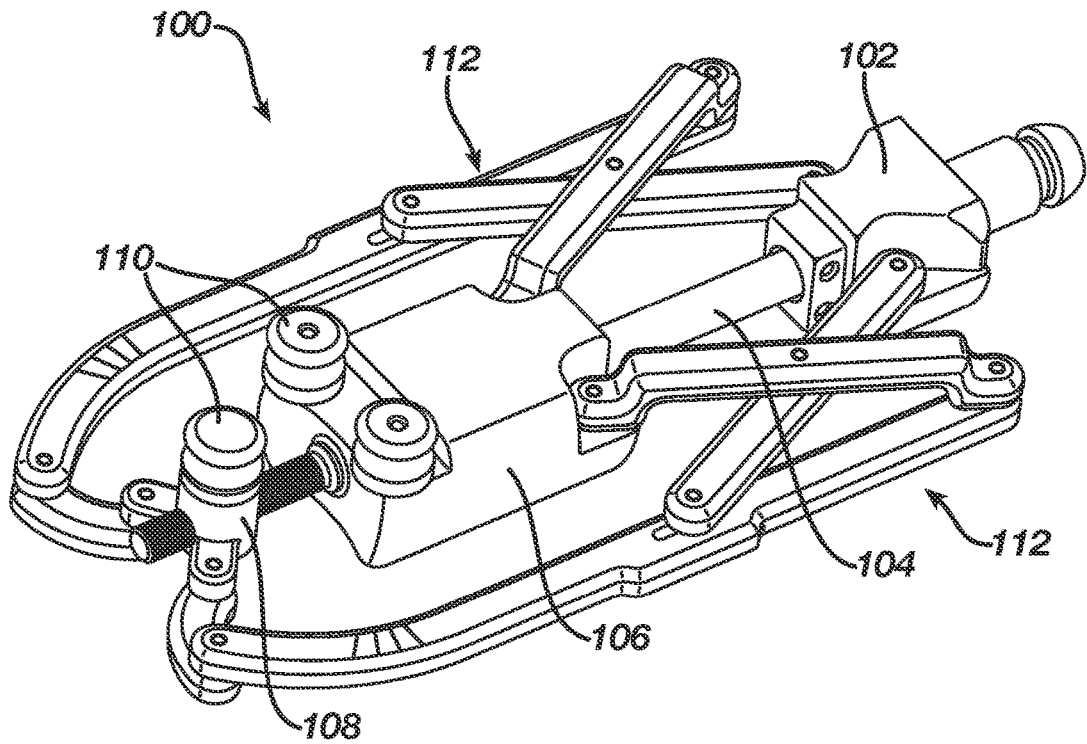
FIG. 1 is a perspective view of an exemplary instrument for bending or cutting an implant.
Figure 2:
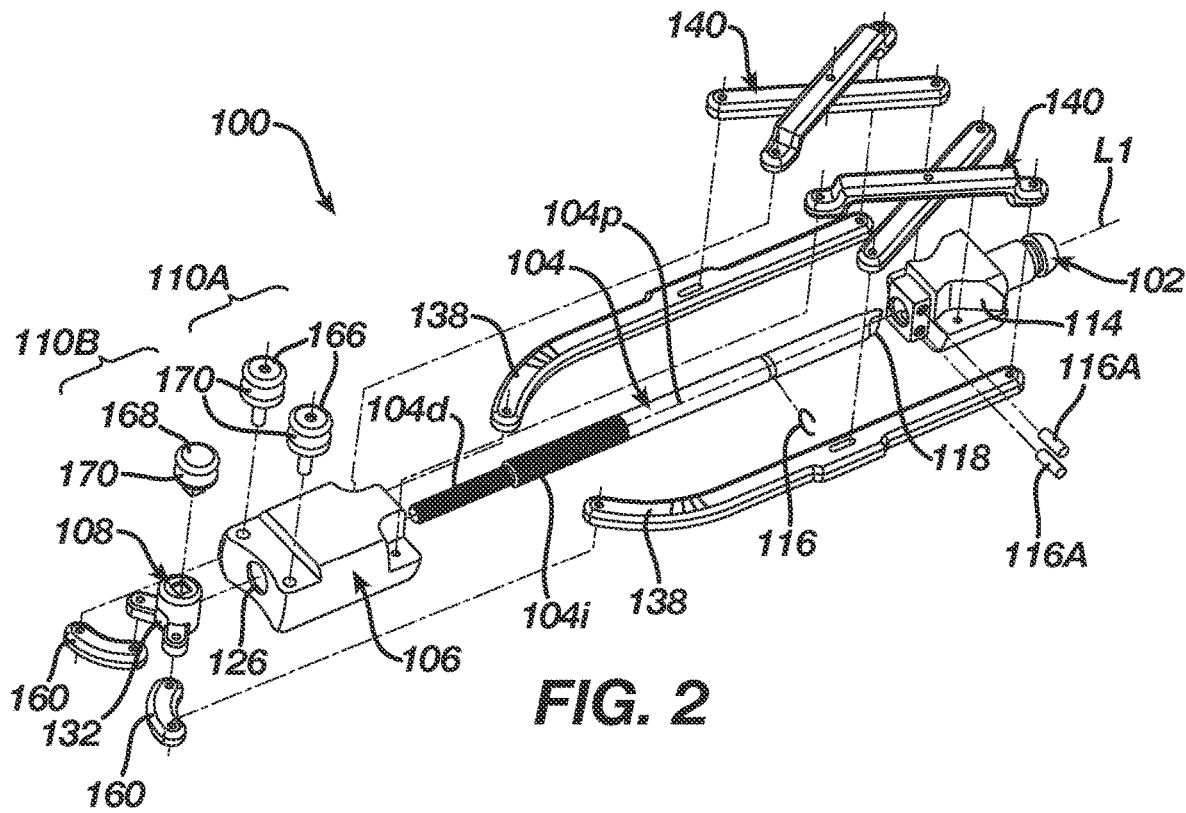
FIG. 2 is an exploded perspective view of the instrument of FIG. 1.
Figure 3:
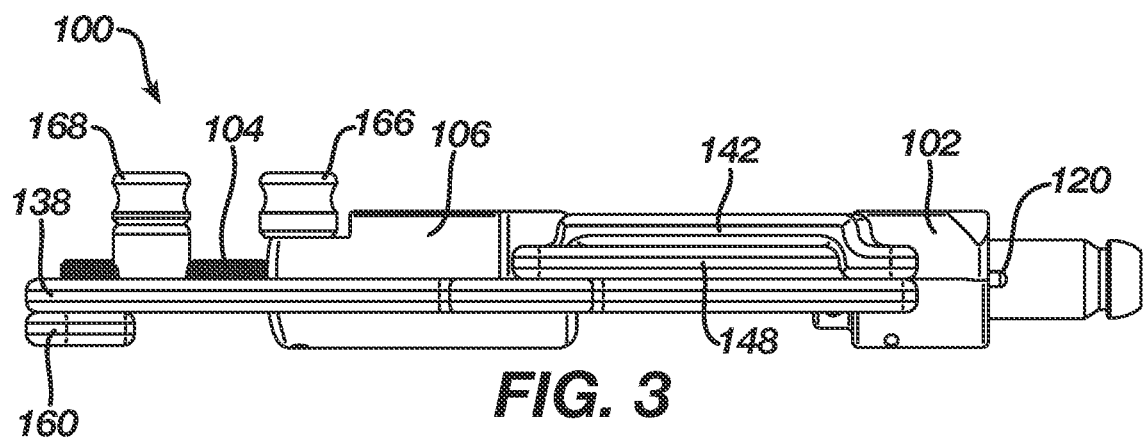
FIG. 3 is a lateral profile view of the instrument of FIG. 1.
Figure 4:
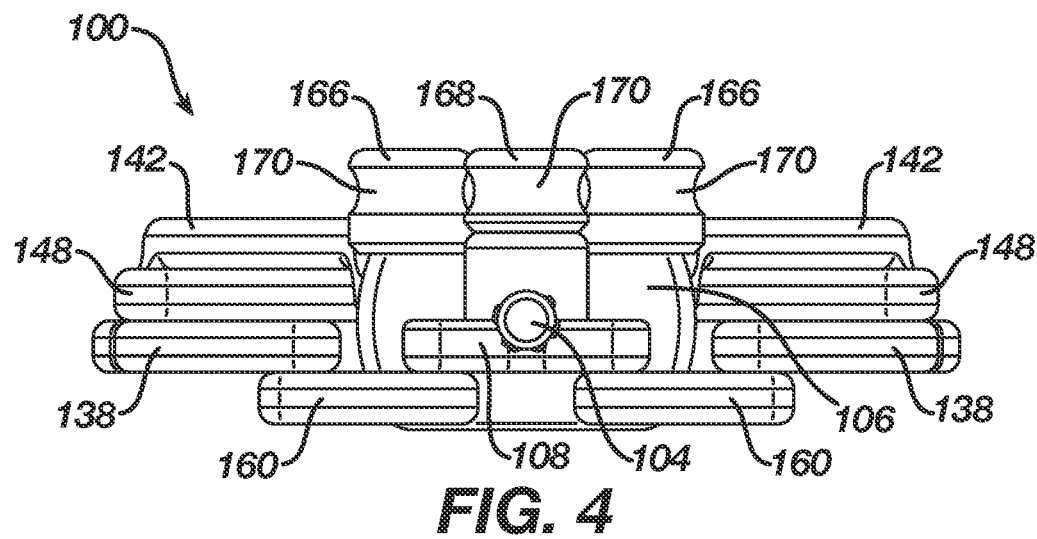
FIG. 4 is an end profile view of the instrument of FIG. 1.

Devices and methods for bending or cutting implants are disclosed herein. In some embodiments, an instrument can include a rotatable drive shaft that urges first and second portions of a modular bending or cutting template toward one another to bend or cut an implant disposed between the template portions. A linkage assembly can be included to provide a mechanical advantage in urging the template portions toward one another. In some embodiments, an instrument can include a rotatable drive shaft that, depending on direction of rotation, pushes or pulls a first modular template portion with respect to a second modular template portion to bend an implant disposed between the template portions in one direction or another direction. In some embodiments, an instrument can include a worm drive that rotates a cutting wheel with respect to a cutting plate to cut an implant inserted through openings formed in the cutting wheel and the cutting plate.

Certain exemplary embodiments will now be described to provide an overall understanding of the principles of the structure, function, manufacture, and use of the devices and methods disclosed herein. One or more examples of these embodiments are illustrated in the accompanying drawings. Those of skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

FIGS. 1-9 illustrate an exemplary embodiment of an instrument 100 which can be used, for example, to bend or cut an implant.

The instrument 100 generally includes an adapter 102, a drive shaft 104, a body 106, a pusher 108, a bending or cutting template 110, and a linkage assembly 112. In use, the drive shaft 104 can be rotated to pull the pusher 108 and the body 106 towards one another to bend or cut an implant disposed in the template 110. The linkage assembly 112 can provide a mechanical advantage, helping to pull the pusher 108 and the body 106 towards one another.

The adapter 102 can include a housing 114 in which a proximal end of the drive shaft 104 is rotatably disposed. A retention ring or washer 116 can be mounted in corresponding grooves formed in the drive shaft 104 and the interior of the adapter housing 114 to maintain the drive shaft at a fixed longitudinal position with respect to the housing. Alternatively, or in addition, one or more dowel pins 116A can be mounted in the adapter housing 114 and seated in a groove formed in the drive shaft 104. A proximal end of the adapter 102 can include a mating feature for coupling the adapter to a driver tool (e.g., a manual, electric, hydraulic, or pneumatic drill or driver tool). An exemplary battery-powered driver tool is described below and shown in FIG. 25. The illustrated adapter 102 is configured for use with a driver tool that includes a rotating component sized to fit within a proximal cylindrical opening of the adapter housing to engage a drive feature 118 formed at the proximal end of the drive shaft 104. The adapter housing 114 is non-rotatably coupled to a non-rotating component of the driver tool. Accordingly, when the driver tool is actuated, the drive shaft 104 rotates relative to a handle portion of the driver tool while the adapter housing 114 remains stationary with respect to the handle portion of the driver tool. The adapter housing 114 can include one or more pins or other anti-rotation features 120 to prevent the adapter housing from rotating relative to the driver tool. The adapter housing 114 can include one or more attachment points at which the housing is coupled to the linkage assembly 112. In the illustrated embodiment, the housing 114 is coupled to the linkage assembly 112 via first and second pivot pins 122, 124.

The drive shaft 104 can be an elongate cylindrical rod having a proximal portion 104$p$, an intermediate portion 104$i$, and a distal portion 104$d$. The proximal portion 104$p$ of the drive shaft 104 can include a drive feature 118 formed at a terminal end thereof configured to be engaged by a rotating component of a driver tool such that the driver tool can be used to rotate the drive shaft. The intermediate portion 104$i$ of the drive shaft 104 can include a threaded exterior surface that is threadably mounted within the body 106. The distal portion 104$d$ of the drive shaft 104 can include a threaded exterior surface that is threadably mounted within the pusher 108. In some embodiments, the intermediate and distal portions 104$i$, 104$d$ of the drive shaft 104 can have opposite threads (e.g., left hand vs. right hand) of the same pitch such that rotation of the drive shaft in a first direction is effective to pull the pusher 108 and the body 106 towards one another and such that rotation of the drive shaft in a second, opposite direction is effective to pull the pusher and the body away from one another.

The body 106 can include a central bore or through-hole 126 that extends longitudinally through the body. The drive shaft 104 can be rotatably received within the central bore 126. The central bore 126 can include an internal thread configured to engage with the external thread of the intermediate portion 104$i$ of the drive shaft 104. A proximal end of the body 106 can include one or more attachment points at which the body is coupled to the linkage assembly 112. In the illustrated embodiment, the body 106 is coupled to the linkage assembly 112 via first and second pivot pins 128, 130. A distal end of the body 106 can include one or more attachment points at which the body is coupled to a first portion of the template 110.

The pusher 108 can include a central bore or through-hole 132 that extends longitudinally through the pusher 108. The drive shaft 104 can be rotatably received within the central bore 132. The central bore 132 can include an internal thread configured to engage with the external thread of the distal portion 104d of the drive shaft 104. A distal end of the pusher 108 can include one or more attachment points at which the pusher is coupled to the linkage assembly 112. In the illustrated embodiment, the pusher 108 is coupled to the linkage assembly 112 via first and second pivot pins 134, 136. A proximal end of the pusher 108 can include one or more attachment points at which the pusher is coupled to a second portion of the template 110.

The linkage assembly 112 can be configured to provide a mechanical advantage to assist in pulling the pusher 108 and the body 106 towards or away from one another. The linkage assembly 112 can also be configured to prevent rotation of the pusher 108, the template 110, and the body 106 with respect to the adapter housing 114. In particular, the linkage assembly 112 can be configured to prevent rotation of the pusher 108, the template 110, and the body 106 about a central longitudinal axis L1 of the adapter 102 during actuation of the instrument 100.

The illustrated linkage assembly 112 generally includes first and second curved arms 138 which are each coupled to the body 106 and to the adapter 102 by a corresponding scissor linkage 140. Each scissor linkage 140 includes a first scissor link 142 having a distal end coupled to an attachment point on the body 106 (e.g., via a pivot pin 128 or 130) and a proximal end coupled to an attachment point on the curved arm 138 (e.g., via a pivot pin 144 or 146 mounted at the proximal end of the curved arm). Each scissor linkage 140 also includes a second scissor link 148 having a proximal end coupled to an attachment point on the adapter 102 (e.g., via a pivot pin 122 or 124) and a distal end slidably coupled to an attachment point on the curved arm 138 (e.g., via a pivot pin 150 or 152 mounted in a longitudinally-elongated slot 154 formed in a portion of the curved arm intermediate the proximal and distal ends thereof). The first and second scissor links 142, 148 are also pivotally coupled to one another via pivot pins 156, 158.

The first and second curved arms 138 are coupled to the pusher 108 by corresponding first and second distal links 160. Each distal link 160 includes a proximal end coupled to an attachment point on the pusher 108 (e.g., via a pivot pin 134 or 136) and a distal end coupled to an attachment point on the curved arm 138 (e.g., via a pivot pin 162 or 164 mounted at the distal end of the curved arm).

Figure 5:
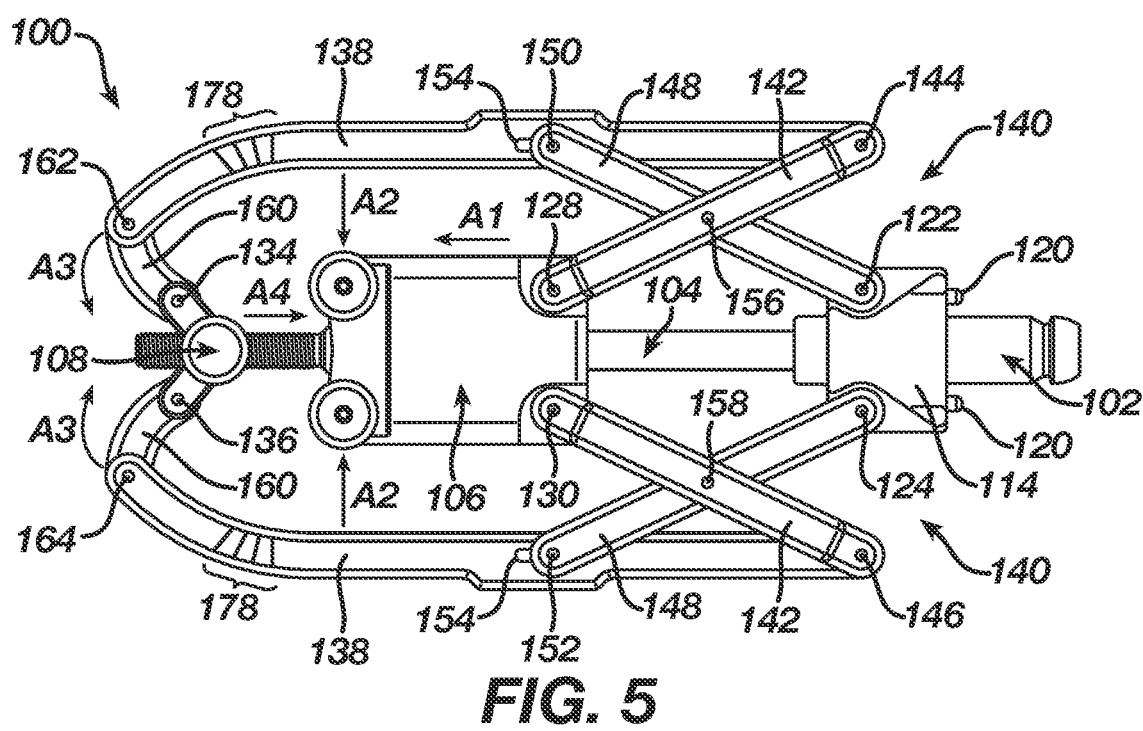
FIG. 5 is a plan view of the instrument of FIG. 1.

In use, as shown in FIG. 5, rotation of the drive shaft 104 in a first direction pushes the body 106 distally away from the adapter housing 114 in the direction of the arrow A1. This movement closes the scissor linkages 140 to pull the first and second curved arms 138 inward towards the drive shaft 104 in the direction of the arrows A2. Inward movement of the first and second curved arms 138 rotates the distal links 160 in the direction of the arrows A3, which in turn urges the pusher 108 towards the body 106 in the direction of the arrow A4. The linkage assembly 112 thus converts rotational movement of the drive shaft 104 into linear movement of the pusher 108 and the body 106 towards one another and amplifies the force of said linear movement by a lever-type mechanical advantage.

It will be appreciated that the linkage assembly 112 shown and described above is merely exemplary and that any of a variety of linkage assemblies can be used instead or in addition. For example, in some embodiments, the pivot pin and elongated slot coupling used to attach the second scissor links 148 to the curved arms 138 can be replaced with a tube formed at the distal end of the scissor link in which the curved arm is slidably disposed. Such an arrangement can, in some instances, provide a coupling that is less susceptible to wear. By way of further example, the distal links 160 can be eliminated in some embodiments, with the curved arms 138 instead being directly coupled to the pusher 108 and the pusher being stationary. This can allow for a lower-profile device that can more-easily fit down into a surgical opening formed in a patient. As yet another example, the locations of the pivot points at which the scissor links 142, 148 attach to the curved arms 138 and/or the length of the various links can be selected to increase or decrease the mechanical advantage provided by the linkage assembly 112.

The template 110 can have any of a variety of configurations depending on the type of bend or cut to be formed, the type or size of implant which is to be bent or cut, or various other factors. The instrument 100 can include a plurality of interchangeable or modular templates 110 to facilitate use of the instrument for any of a variety of tasks. In other embodiments, the template 110 can be permanently fixed to the instrument 100. By way of example, templates can be provided that are formed from different materials, formed with bend surfaces having different curvatures, and/or formed with bend recesses having different diameters. Templates with flat bend surfaces can also be provided, e.g., for use in bending bone plates or other implants. In some embodiments, the instrument 100 can be provided as part of a kit that includes a plurality of modular templates 110.

The template 110 generally includes first and second portions 110A, 110B. The first portion 110A can be configured to be selectively coupled to the body and the second portion can be configured to be selectively coupled to the pusher 108, or the first and second portions can be interchangeably attachable to either of the body or the pusher. The first and second portions 110A, 110B can be coupled to the instrument 100 using any of a variety mating features. For example, each portion 110A, 110B of the template can include a male mating feature configured to be received within a corresponding female mating feature of the instrument 100 or vice versa. A circlip, ball plunger, or other retention mechanism can also be included in or on the mating features. By way of further example, each portion 110A, 110B of the template can engage the instrument 100 via a snap-fit interface, a press-fit interface, a threaded interface, or the like. As yet another example, the template 110 components can be screwed or bolted to the instrument 100. In some embodiments, the template 110 components can be rotatably coupled to the instrument 100.

An exemplary template 110 for bending an implant (e.g., a cylindrical rod) is shown in FIGS. 1-5. As shown, the first portion 110A of the template includes first and second cylindrical rollers or bending blocks 166 that engage the implant along an outside portion of the bend to be formed. The second portion 110B of the template includes a third cylindrical roller or bending block 168 that engages the implant along an inside portion of the bend to be formed. Each of the first, second, and third bending blocks can include an annular concavity or recess 170 sized to receive at least a portion of the implant therein. For example, the bending blocks 166, 168 can include a toroidal recess having a radius substantially equal to the radius of the implant which is to be bent using the instrument 100. The instrument 100 can thus include a plurality of templates 110 having different recess radii, each being configured for use with a different diameter implant (e.g., a 3.5 mm rod, a 4.5 mm rod, a 5.5 mm rod, a 6.35 mm rod, etc.) The bending blocks 166, 168 can be rotatably mounted in the instrument 100 to allow them to roll along the implant as the implant is bent. It will be appreciated that the attachment location of the first and second components 110A, 110B of the template can be flipped such that the first portion of the template is instead coupled to the pusher 108 and the second portion of the template is instead coupled to the body 106. This can be particularly useful when bending an implant that is at least partially implanted in a patient, as it can allow the user to bend the implant in the desired direction when the approaches to the implant are limited by patient anatomy or other obstacles.

Figure 6:
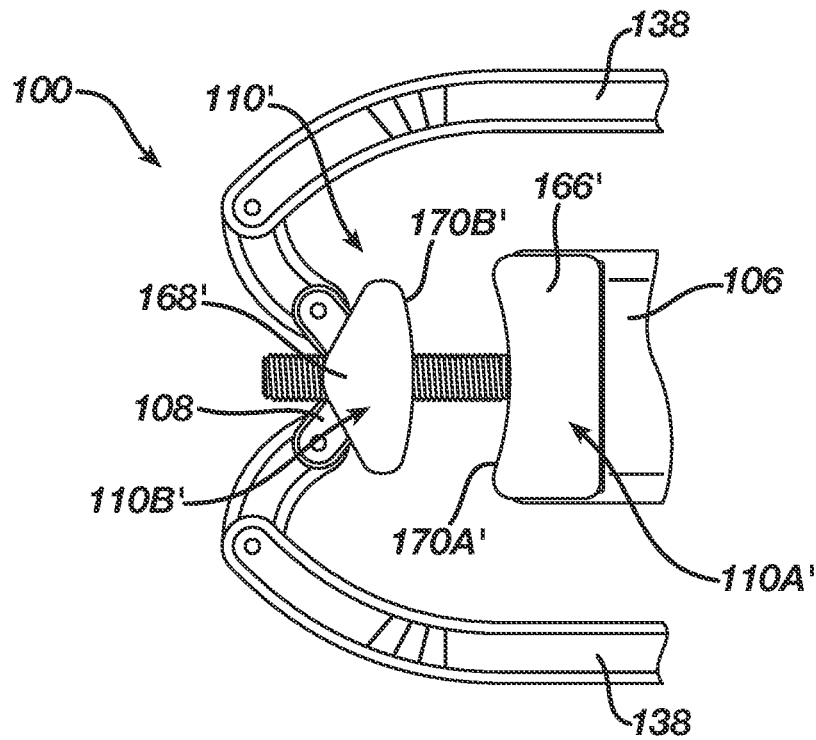
FIG. 6 is a plan view of the instrument of FIG. 1 with an alternate bending template.
Figure 7:
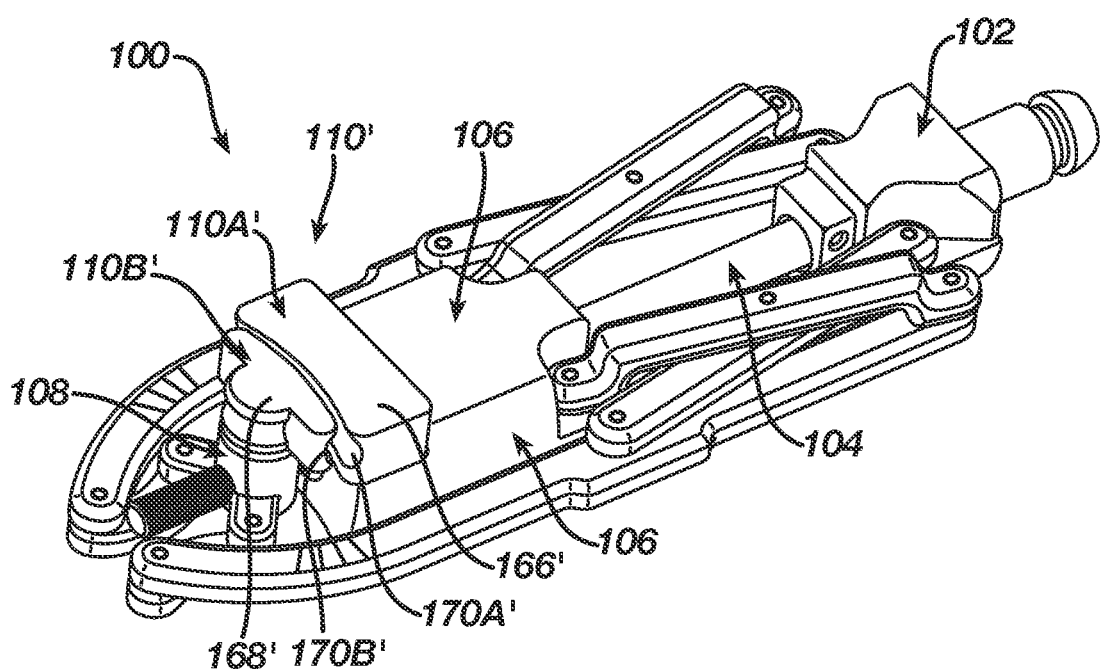
FIG. 7 is a perspective view of the instrument and template of FIG. 6.

FIGS. 6-7 illustrate another exemplary template 110' for bending an implant (e.g., a cylindrical rod). As shown, the first portion 110A' of the template includes a substantially rectangular bending block 166' with a recess 170A' formed in a distal-facing surface thereof. The recess 170A' defines a negative of the outside portion of a bend to be formed in the implant. The second portion 110B' of the template includes a bending block 168' with a corresponding recess 170B' formed in a proximal-facing surface thereof. The recess 170B' defines a negative of the inside portion of a bend to be formed in the implant. It will be appreciated that the attachment location of the first and second components 110A', 110B' of the template can be flipped such that the first portion of the template is instead coupled to the pusher 108 and the second portion of the template is instead coupled to the body 106.

Figure 8:
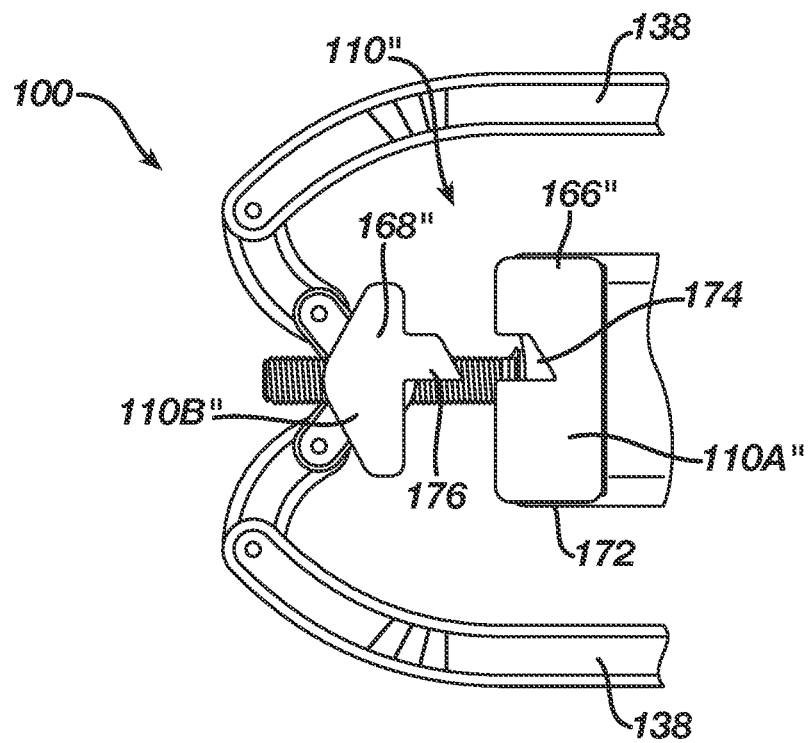
FIG. 8 is a plan view of the instrument of FIG. 1 with a cutting template.
Figure 9:
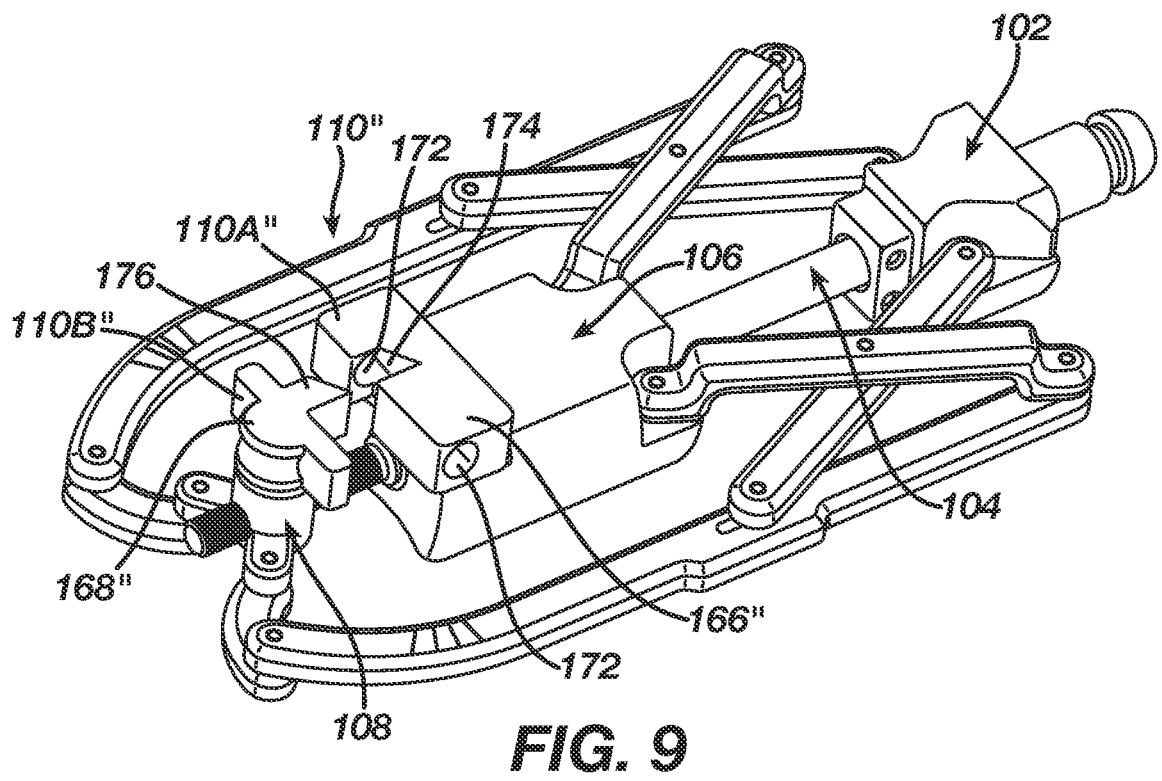
FIG. 9 is a perspective view of the instrument and template of FIG. 8.
Figure 10:
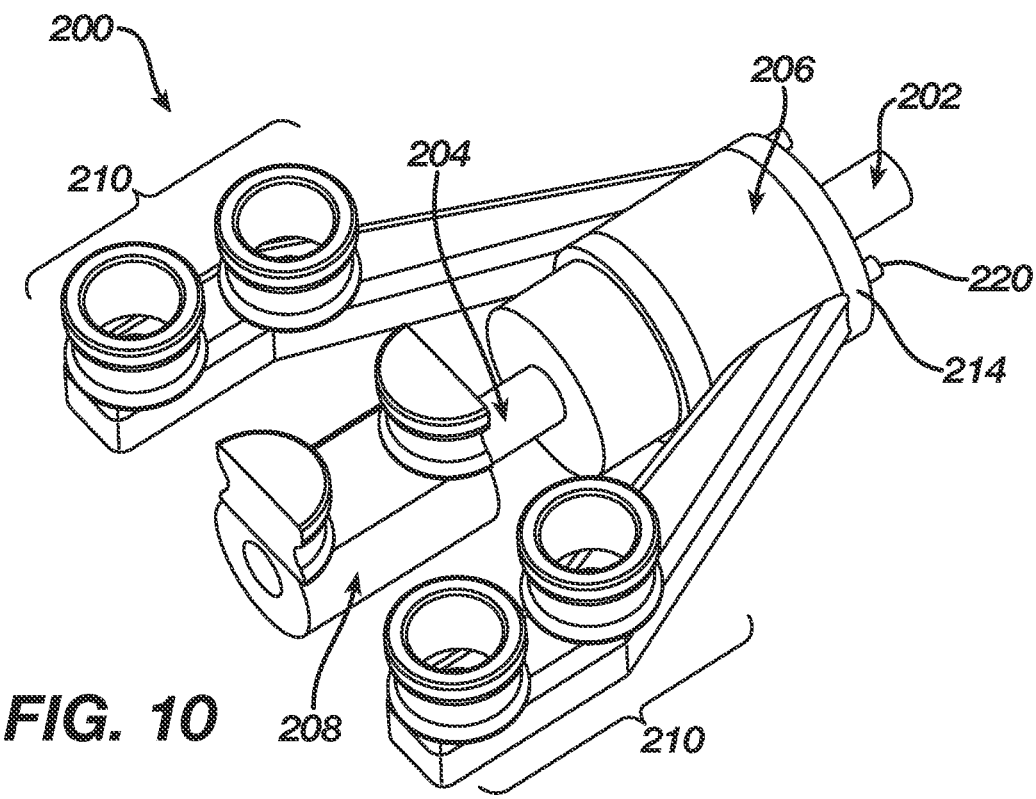
FIG. 10 is a perspective view of an exemplary instrument for bending or cutting an implant.
Figure 11:
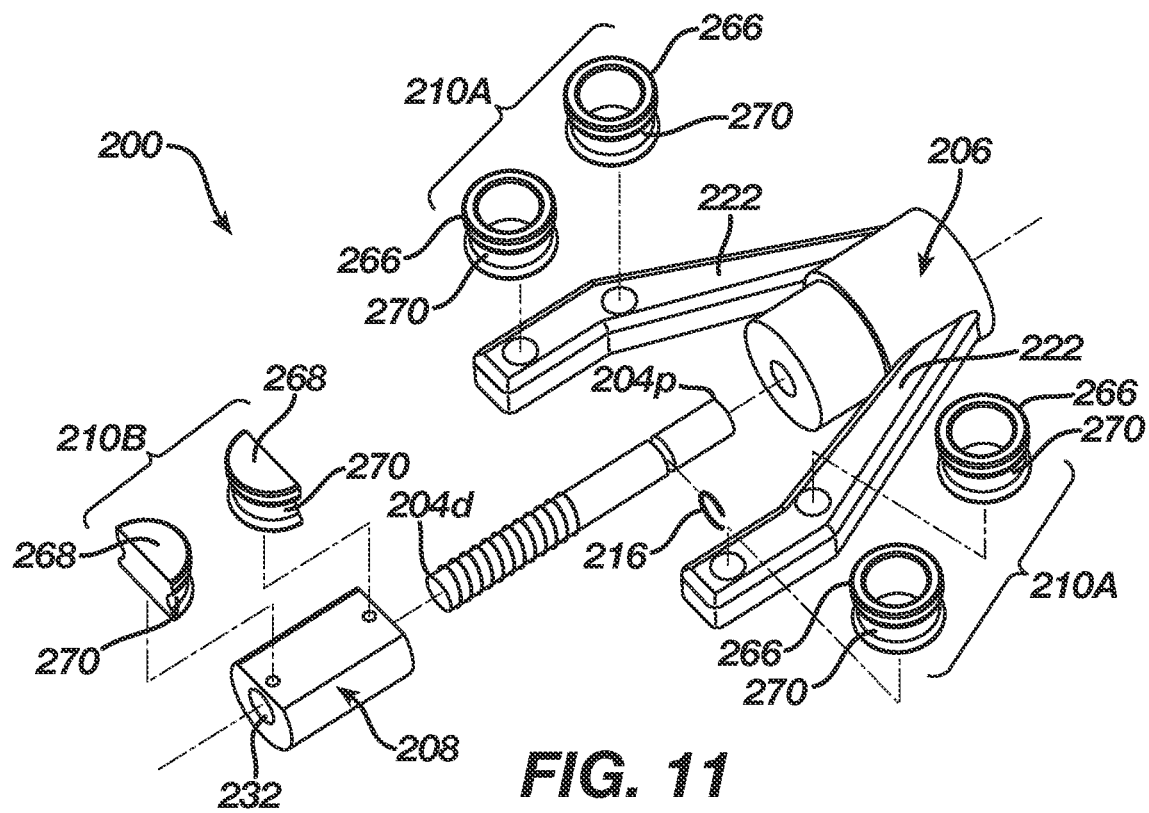
FIG. 11 is an exploded perspective view of the instrument of FIG. 10.

FIGS. 8-9 illustrate an exemplary template 110" for cutting an implant (e.g., a cylindrical rod). As shown, the first portion 110A" of the template includes a cutting block 166" that defines a longitudinal cylindrical through-bore 172 in which the implant can be disposed. The through-bore 172 can be sized based on the diameter of the implant that is to be cut using the instrument 100. In some embodiments, the instrument 100 can include a plurality of cutting blocks 166", each configured for use with an implant having a different diameter (e.g., 3.5 mm, 4.5 mm, 5.5 mm, and/or 6.35 mm rods). The through-bore 172 can also be open to one or more sides of the cutting block 166" to allow insertion of an implant from the side (e.g., in the case of a spinal rod or other implant that is already at least partially implanted in a patient). The cutting block 166" also includes a lateral recess 174 that intersects the longitudinal through-bore 172. The second portion 110B" of the template includes a cutting block 168" with a blade or knife 176 extending therefrom. The blade 176 is sized to be received within the lateral recess 174 of the first portion 110A" of the template as the first and second portions 110A", 110B" are pulled towards one another to sever an implant disposed within the cylindrical through-bore 172. The portions of the cutting block 166" on either side of the lateral recess 174 can advantageously hold the cut ends of the implant in place to prevent the implant from shifting suddenly when it is cut and injuring the user or nearby patient tissue. While not shown, the cutting block 166" can include a locking mechanism (e.g., a ball plunger, donut spring, wing nut, screw, or clamp) configured to positively engage the cut portions of the implant to prevent them from slipping out of the cutting block.

In use, the instrument 100 can be used to bend or cut an implant. An implant (e.g., a bone plate or spinal rod) can be positioned between the first and second portions 110A, 110B of the bending or cutting template 110. The drive shaft 104 can be rotated relative to the adapter housing 114 to push the body 106 distally away from the adapter housing and pull the pusher 108 towards the adapter housing via the linkage assembly 112. The first and second portions 110A, 110B of the template can thus apply a bending or cutting force to the implant.

The degree to which the implant is bent can be selected by controlling the number of times the drive shaft 104 rotates and thus the distance that the pusher 108 and body 106 travel towards one another. In some embodiments, the drive shaft 104 can include markings or other indicia to indicate to a user the length of travel or bend angle/radius. Alternatively, or in addition, the curved arms 138 can include markings or indicia 178 to indicate to a user the degree to which an implant has been bent. The indicia can be calibrated to the physical dimensions of the instrument 100 such that a consistent and accurate bend having a desired angle or bend radius can be achieved by simply actuating the instrument 100 until the implant is aligned with the indicia associated with said desired angle or bend radius (e.g., in the case of indicia on the curved arms 138) or until the body or pusher is aligned with such indicia (e.g., in the case of indicia on the drive shaft 104). After forming an initial bend in the implant, the implant can be repositioned (e.g., translated or rotated) with respect to the instrument 100 to form additional bends, to form a complex or compound bend shape, or to increase or decrease the degree of a previously-formed bend. It will be appreciated that the position of the pusher 108 and/or the body 106 can be adjusted before inserting the implant into the instrument 100 to accommodate an implant that already includes one or more bends. In some embodiments, a first bend can be formed in the implant using a first template and then the first template can be replaced with a second template to form a second bend in the implant.

In some embodiments, the instrument 100 can be used to bend an implant that is at least partially implanted in a patient. For example, an exemplary method can include coupling a spinal rod to at least one bone anchor disposed in a vertebra of a patient and, while the rod is coupled to the bone anchor, engaging the rod with the instrument 100 and actuating the instrument to bend the rod. Another exemplary method can include coupling a bone plate to at least one bone of a patient and, while the plate is coupled to the bone, engaging the plate with the instrument 100 and actuating the instrument to bend the plate.

FIGS. 10-19 illustrate another exemplary embodiment of an instrument 200 which can be used, for example, to bend or cut an implant.

The instrument 200 generally includes an adapter 202, a drive shaft 204, a body 206, a pusher 208, and a bending or cutting template 210. In use, the drive shaft 204 can be rotated to pull the pusher 208 towards the body 206 or push the pusher away from the body to bend or cut an implant disposed in the template 210.

The adapter 202 can include a housing 214 in which a proximal end 204p of the drive shaft 204 is rotatably disposed. A retention ring or washer 216 can be mounted in corresponding grooves formed in the drive shaft 204 and the interior of the adapter housing 214 to maintain the drive shaft at a fixed longitudinal position with respect to the housing. A proximal end of the adapter 202 can include a mating feature for coupling the adapter to a driver tool (e.g., a manual, electric, hydraulic, or pneumatic drill or driver tool). An exemplary battery-powered driver tool is described below and shown in FIG. 25. The illustrated adapter 202 is configured for use with a driver tool that includes a rotating component sized to fit within a proximal cylindrical opening of the adapter housing to engage a drive feature formed at the proximal end 204p of the drive shaft 204. The adapter housing 214 is non-rotatably coupled to a non-rotating component of the driver tool. Accordingly, when the driver tool is actuated, the drive shaft 204 rotates relative to a handle portion of the driver tool while the adapter housing 214 remains stationary with respect to the handle portion of the driver tool. The adapter housing 214 can include one or more pins or other anti-rotation features 220 to prevent the adapter housing from rotating relative to the driver tool.

The drive shaft 204 can be an elongate cylindrical rod having a proximal portion 204p and a distal portion 204d. The proximal portion 204p of the drive shaft can include a drive feature formed at a terminal end thereof configured to be engaged by a rotating component of a driver tool such that the driver tool can be used to rotate the drive shaft. The distal portion 204d of the drive shaft can include a threaded exterior surface that is threadably mounted within the pusher 208. Accordingly, rotation of the drive shaft 204 in a first direction can be effective to pull the pusher 208 towards the body 206 (along the longitudinal axis of the drive shaft 204) and rotation of the drive shaft in a second, opposite direction can be effective to push the pusher away from the body.

The body 206 can be formed integrally with the adapter housing 214, or can be a separate component coupled thereto. The body 206 can include first and second arms 222 that extend distally from the body. The arms 222 can be formed integrally with the main portion of the body 206 as shown, or can be separate components coupled thereto using any of a variety of techniques which will be readily appreciated, as discussed further below. The distal ends of the arms 222 can include one or more attachment points at which the body is coupled to a first portion of the template 210.

The pusher 208 can include a central bore or through-hole 232 that extends longitudinally through the pusher. The drive shaft 204 can be rotatably received within the central bore 232. The central bore can include an internal thread configured to engage with the external thread of the distal portion 204d of the drive shaft 204. The pusher 208 can include one or more attachment points at which the pusher is coupled to a second portion of the template 210.

The template 210 can have any of a variety of configurations depending on the type of bend or cut to be formed, the type or size of implant which is to be bent or cut, or various other factors. The instrument 200 can include a plurality of interchangeable or modular templates 210 to facilitate use of the instrument for any of a variety of tasks. In other embodiments, the template 210 can be permanently fixed to the instrument 200. By way of example, templates 210 can be provided that are formed from different materials, formed with bend surfaces having different curvatures, and/or formed with bend recesses having different diameters. Templates 210 with flat bend surfaces can also be provided, e.g., for use in bending bone plates or other implants. In some embodiments, the instrument 200 can be provided as part of a kit that includes a plurality of modular templates 210.

The template 210 generally includes first and second portions 210A, 210B. The first portion 210A can be configured to be selectively coupled to the body 206 (e.g., via the arms 222) and the second portion 210B can be configured to be selectively coupled to the pusher 208, or the first and second portions can be interchangeably attachable to either of the body or the pusher. The first and second portions 210A, 210B can be coupled to the instrument 200 using any of a variety mating features. For example, each portion 210A, 210B of the template can include a male mating feature configured to be received within a corresponding female mating feature of the instrument 200 or vice versa. A circlip, ball plunger, or other retention mechanism can also be included in or on the mating feature. By way of further example, each portion of the template 210A, 210B can engage the instrument 200 via a snap-fit interface, a press-fit interface, a threaded interface, or the like. As yet another example, the template 210 components can be screwed or bolted to the instrument 200. In some embodiments, the template 210 components can be rotatably coupled to the instrument 200.

An exemplary template 210 for bending an implant (e.g., a cylindrical rod) is shown in FIGS. 10-14. As shown, the first portion 210A of the template includes four cylindrical rollers or bending blocks 266. Specifically, each arm 222 of the body 206 is coupled to respective first and second bending blocks 266 that define a space therebetween sized to receive an implant to be bent. The implant can be positioned within the spaces such that the bending blocks 266 engage the implant at two or more contact points (e.g., points C1 and C2 shown in FIG. 13). The second portion 210B of the template includes two bending blocks 268, at least one of which can engage the implant at a location intermediate to the two or more contact points (e.g., a point C3 shown in FIG. 13). While semi-cylindrical bending blocks 268 are shown, it will be appreciated that the bending blocks can be cylindrical or have any other shape. Each of the bending blocks 266, 268 can include an annular concavity or recess 270 sized to receive at least a portion of the implant therein. For example, the bending blocks 266, 268 can include a toroidal recess 270 having a radius substantially equal to the radius of the implant which is to be bent using the instrument 200. The instrument 200 can thus include a plurality of templates 210 having different recess radii, each being configured for use with a different diameter implant (e.g., a 3.5 mm rod, a 4.5 mm rod, a 5.5 mm rod, a 6.35 mm rod, etc.) The bending blocks 266, 268 can be rotatably mounted in the instrument 200 to allow them to roll along the implant as the implant is bent.

Figure 12:
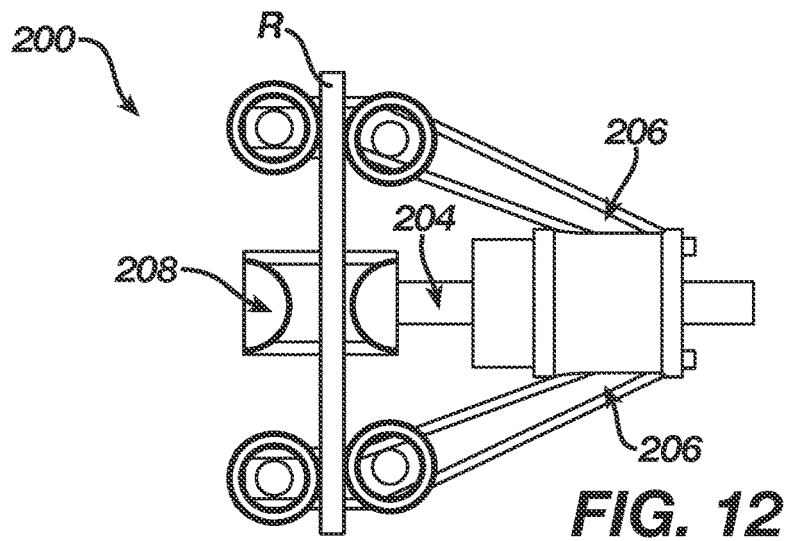
FIG. 12 is a plan view of the instrument of FIG. 10 with an implant positioned therein.
Figure 13:
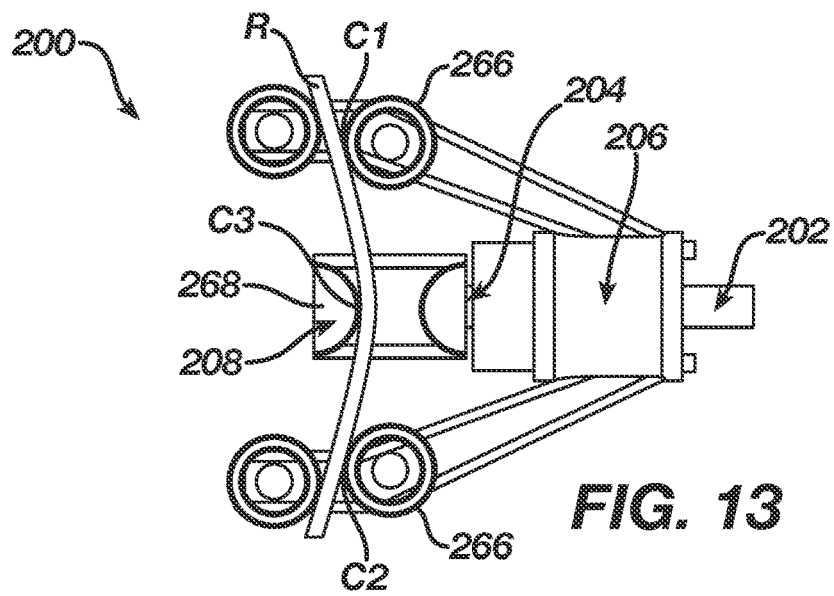
FIG. 13 is a plan view of the instrument of FIG. 10 after bending an implant in a first direction.
Figure 14:
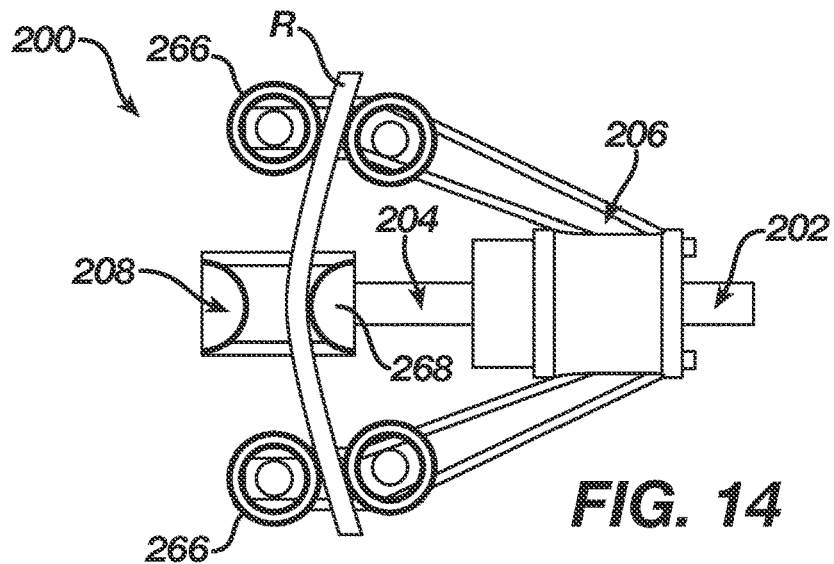
FIG. 14 is a plan view of the instrument of FIG. 10 after bending an implant in a second direction.

In use, an implant R (e.g., a spinal rod or a bone plate) can be positioned between the first and second portions 210A, 210B of the template 210 as shown in FIG. 12. The drive shaft 204 can be rotated with respect to the adapter 202, for example using a manual or power driver, to form a desired bend in the implant R. For example, as shown in FIG. 13, rotation of the drive shaft 204 in a first direction can be effective to pull the pusher 208 towards the body 206 and towards the proximal bending blocks 266 mounted to the body, forming a bend in the implant R. As another example, as shown in FIG. 14, rotation of the drive shaft 204 in a second direction opposite to the first direction can be effective to push the pusher 208 away from the body 206 and towards the distal bending blocks 266 mounted to the body, bending the implant R in the opposite direction.

The degree to which the implant is bent can be selected by controlling the number of times the drive shaft 204 rotates and thus the distance that the pusher 208 travels with respect to the body 206. In some embodiments, the drive shaft 204 can include markings or other indicia to indicate to a user the length of travel or bend angle. After forming an initial bend in the implant, the implant can be repositioned with respect to the instrument 200 to form additional bends, to form a complex or compound bend shape, or to increase or decrease the degree of a previously-formed bend. While an initially-straight implant R is shown in FIG. 12, it will be appreciated that the position of the pusher 208 can be adjusted before inserting the implant into the instrument to accommodate an implant that already includes one or more bends.

In some embodiments, the instrument 200 can be used to bend an implant that is at least partially implanted in a patient. For example, an exemplary method can include coupling a spinal rod to at least one bone anchor disposed in a vertebra of a patient and, while the rod is coupled to the bone anchor, engaging the rod with the instrument and actuating the instrument 200 to bend the rod. Another exemplary method can include coupling a bone plate to at least one bone of a patient and, while the plate is coupled to the bone, engaging the plate with the instrument 200 and actuating the instrument to bend the plate.

In FIGS. 10-14, the implant helps prevent the pusher 208 from rotating with respect to the body 206 and the adapter 202 to ensure that the pusher does not rotate with the drive shaft 204 during actuation of the instrument 200. In some instances, friction between the implant and the bending blocks 266, 268 that arises once the implant is initially engaged by the instrument 200 can be sufficient to prevent rotation of the pusher 208. In other instances, the implant can be received in and engaged by recesses 270 formed in the bending blocks 266, 268 to create an interference that prevents rotation of the pusher 208. In still further instances, the instrument 200 can include a dedicated anti-rotation mechanism to prevent rotation of the pusher 208 with respect to the adapter 202 and the body 206 during actuation of the instrument 200.

Figure 15:
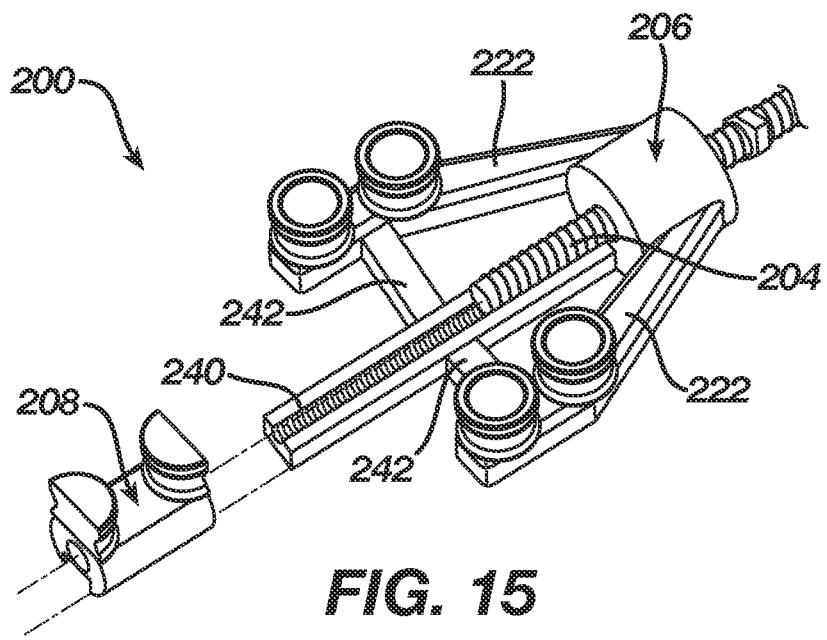
FIG. 15 is a perspective, partially-exploded view of the instrument of FIG. 10 with a central guide rail.

As shown in FIG. 15, the instrument 200 can include an anti-rotation mechanism that includes a guide rail 240 to which the pusher 208 is slidably mounted. The pusher 208 can include a male mating feature that slides within a track formed in the guide rail 240, or can include a female mating feature in which the guide rail 240 is slidably received. The guide rail 240 can extend distally from the body 206, parallel to the drive shaft 204. The guide rail 240 can include one or more support members to resist twisting of the guide rail. For example, the guide rail 240 can include support struts 242 that attach the guide rail to the arms 222 of the body 206.

Figure 16:
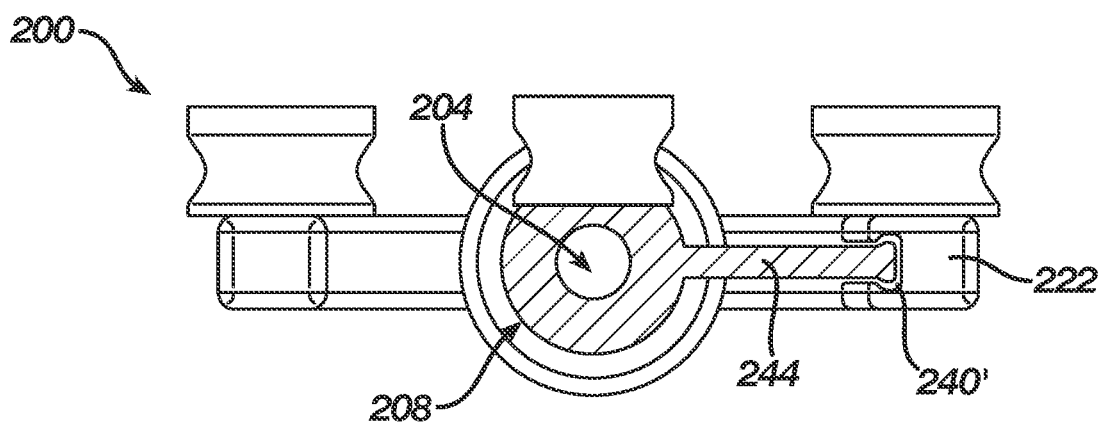
FIG. 16 is an end profile view of the instrument of FIG. 10 with an arm-mounted guide rail.

As shown in FIG. 16, the anti-rotation mechanism can include a guide rail 240' formed integrally with one or both of the arms 222. The guide rail 240' can extend longitudinally along the arm 222, parallel to the drive shaft 204. The pusher 208 can include a male mating feature 244 that projects laterally from the pusher and slides within a track formed in the guide rail 240' of the arm 222 as shown. Alternatively, the lateral projection 244 of the pusher 208 can include a female mating feature in which at least a portion of the guide rail 240' is slidably received.

Figure 17:
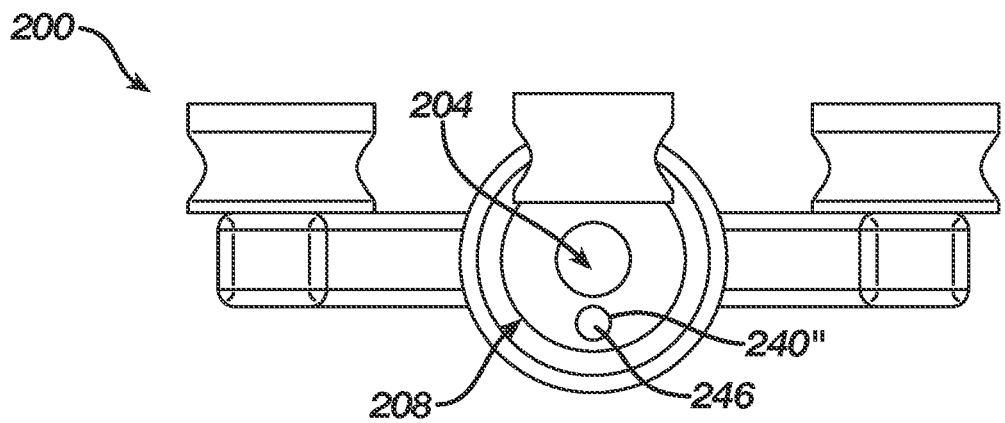
FIG. 17 is an end profile view of the instrument of FIG. 10 with a central guide rod.

As shown in FIG. 17, the anti-rotation mechanism can include a guide rod 240". The guide rod 240" can extend distally from the body 206 and can be received within a cylindrical through-bore 246 formed in the pusher 208 such that the pusher can slide longitudinally along the guide rod. The guide rod 240" can extend parallel to the drive shaft 204 and can be offset from the drive shaft such that the guide rod prevents rotation of the pusher 208 with respect to the adapter 202 and the body 206.

Figure 18:
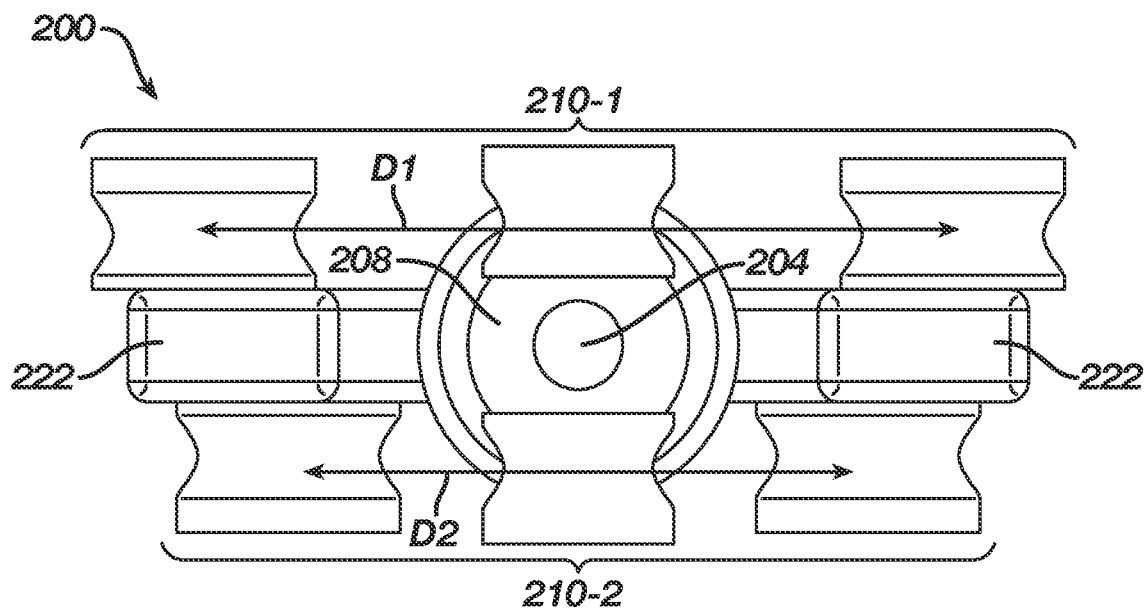
FIG. 18 is an end profile view of the instrument of FIG. 10 with plural bending or cutting templates.

It will be appreciated that the instrument 200 can be used with any of a variety of templates, including any of the templates described above with respect to the instrument 100. The instrument 200 can be configured to selectively couple to any of a plurality of modular cutting or bending templates. In some embodiments, the instrument 200 can be coupled to a plurality of templates simultaneously or can have a plurality of templates fixedly or integrally mounted thereto. For example, as shown in FIG. 18, a first template 210-1 can be mounted on an upper portion of the pusher 208 and the arms 222 while a second template 210-2 is mounted on a lower portion of the pusher and the arms. Such an arrangement can allow a user to change the template that is used for a particular bend or cut by simply choosing which of the two templates to engage the implant with. The first and second templates can have configurations that differ from one another. For example, the first template can be a cutting template and the second template can be a bending template. By way of further example, the first template can be configured for use with implants having a first diameter and the second template can be configured for use with implants having a second diameter that differs from the first diameter. As yet another example, the first template can be configured to form a bend in the implant having a first bend radius and the second template can be configured to form a bend in the implant having a second bend radius that differs from the first bend radius. This can be accomplished, for example, by the first template having a distance D1 between outer bending blocks that differs from the distance D2 between the outer bending blocks of the second template.

Figure 19:
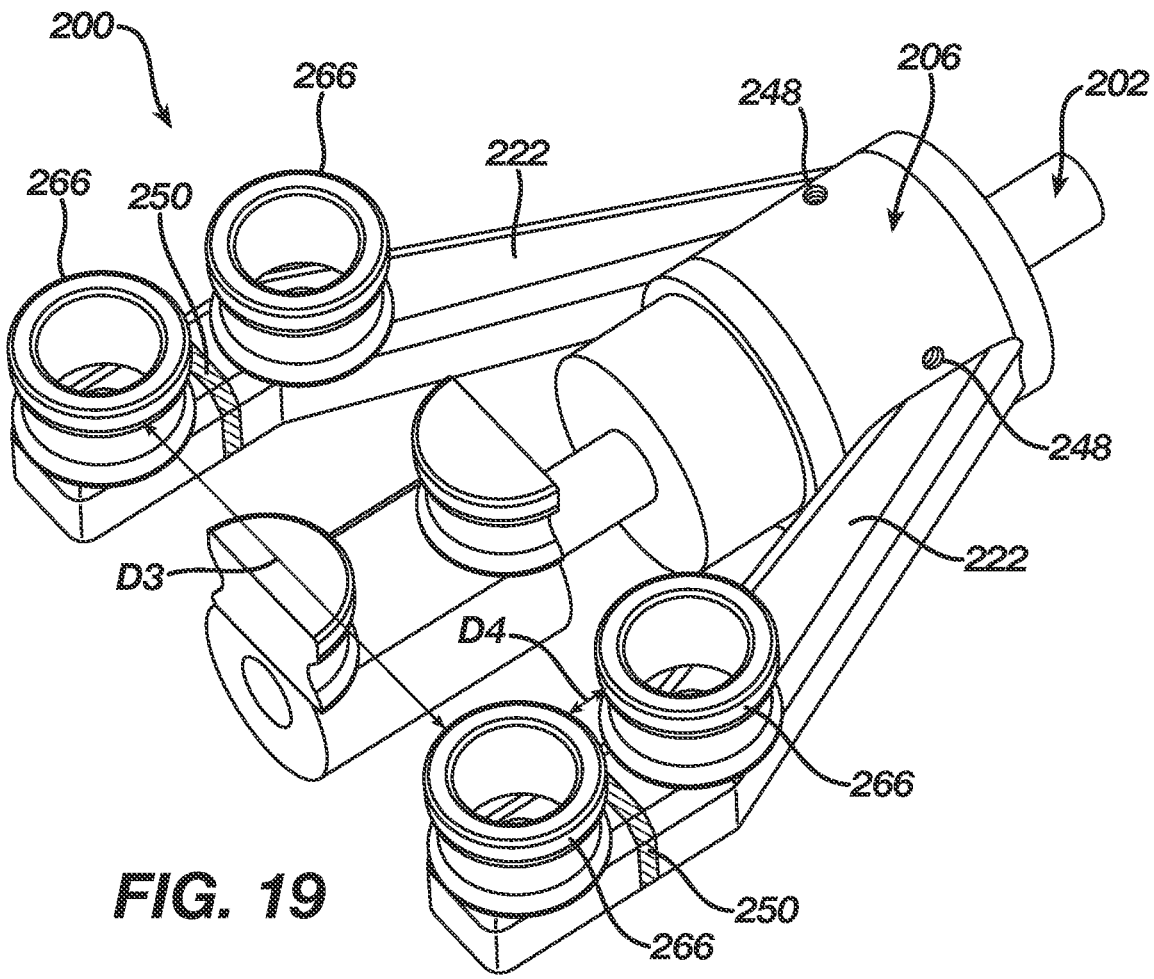
FIG. 19 is a perspective view of the instrument of FIG. 10 with articulating and telescoping arms.
Figure 20:
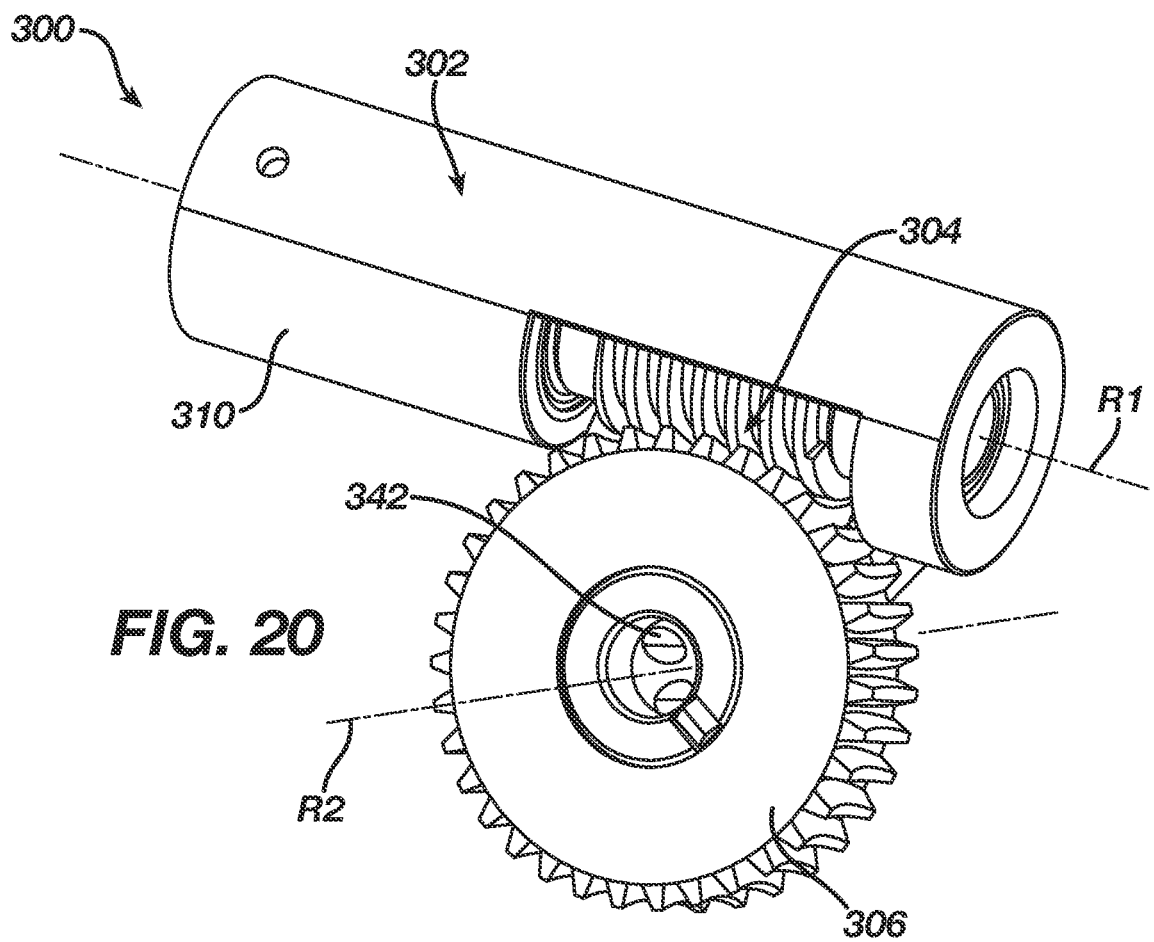
FIG. 20 is a perspective view of an exemplary instrument for cutting an implant.
Figure 21:
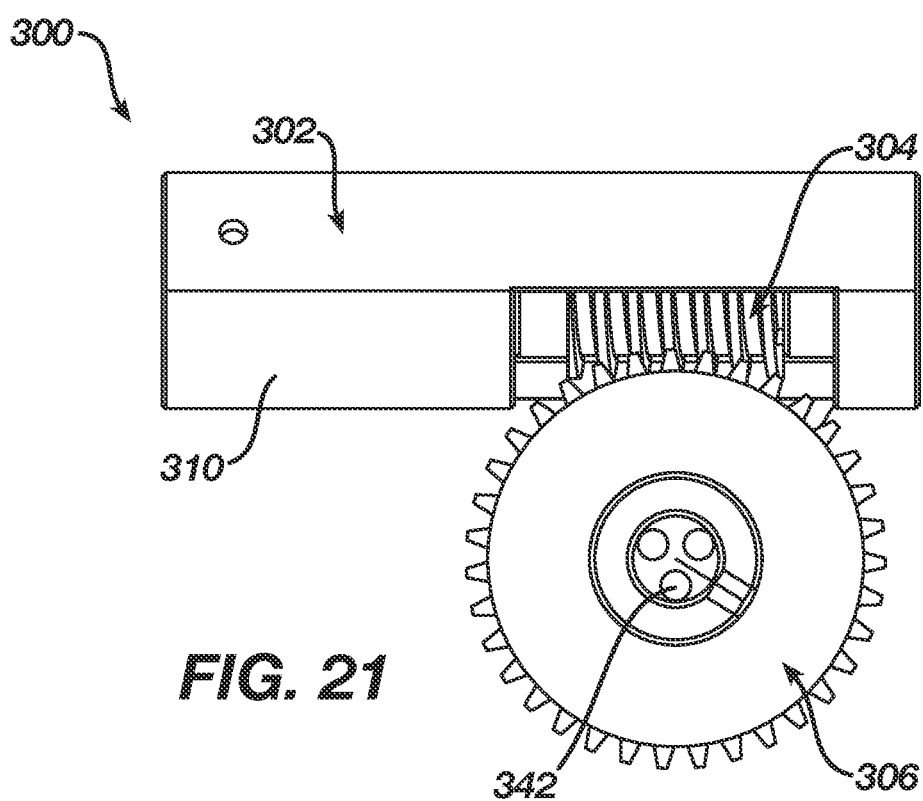
FIG. 21 is a lateral profile view of the instrument of FIG. 20.
Figure 22:
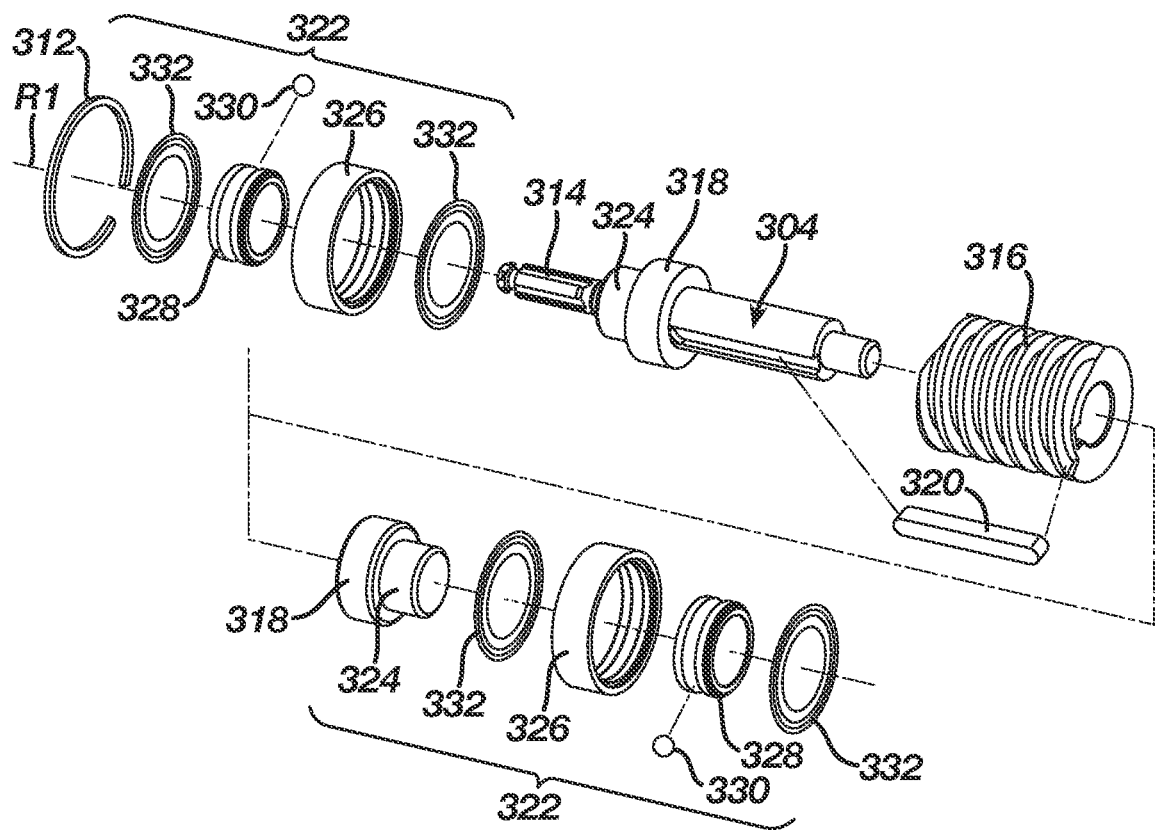
FIG. 22 is an exploded perspective view of the drive shaft, worm screw, and bearing assemblies of the instrument of FIG. 20.
Figure 23:
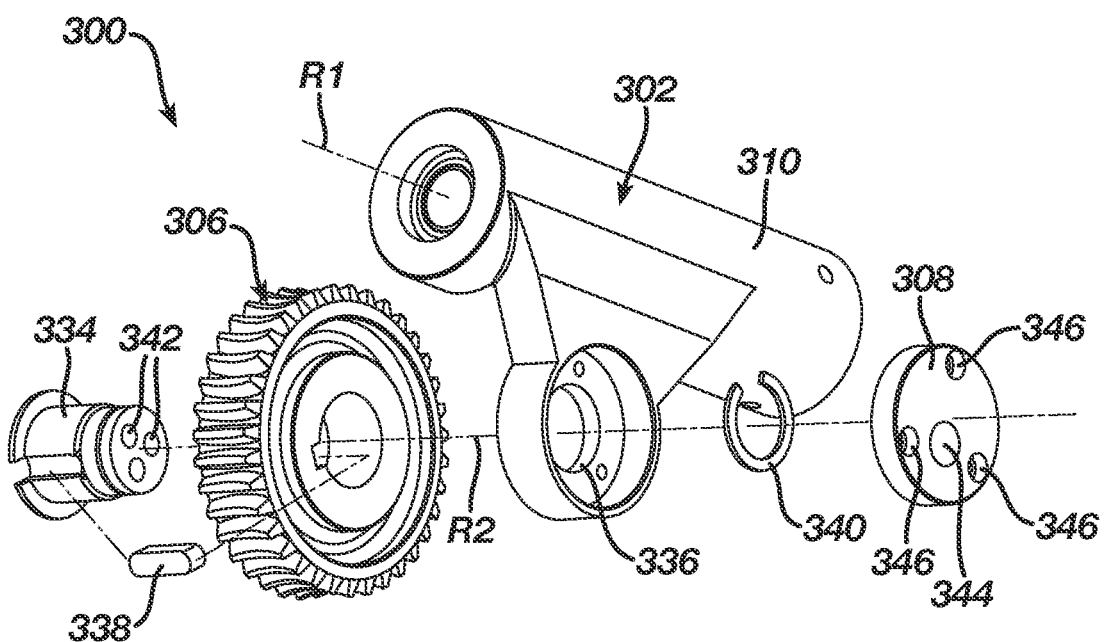
FIG. 23 is an exploded perspective view of the adapter housing, cutting wheel, and cutting plate of the instrument of FIG. 20.

The arms 222 of the instrument 200 or portions thereof can be adjustable with one or more degrees of freedom with respect to the main portion of the body 206 (and thus with respect to the pusher 208) to change one or more parameters of the bend formed by the instrument. For example, as shown in FIG. 19, the arms 222 can be pivotally coupled to the main portion of the body 206 such that a distance D3 between the bending blocks 266 mounted to the arms can be selectively increased or decreased. Adjusting the distance D3 can be effective to adjust the radius of the bend that is formed in an implant using the instrument 200. The arms 222 can be independently adjustable to form an asymmetrical bend, or can be configured to articulate in unison. The arms 222 can be pivotally coupled to the main portion of the body 206 by respective pivot pins 248. A set screw or other locking mechanism can be included to selectively lock the position of the arms 222 with respect to the body 206. In some embodiments, the arms 222 can include a telescoping portion or other longitudinal adjustment feature 250 to allow the length of the arms to be increased or decreased. As shown, the longitudinal adjustment feature 250 can be disposed between the bending blocks 266 such that adjustment of the arm length is also effective to adjust a distance D4 between the bending blocks along the longitudinal axis of the arm (e.g., to accommodate an implant having a greater or lesser diameter between the bending blocks).

The instrument 200 can advantageously bend or cut an implant using either a forward or backward motion of the pusher 208 along the longitudinal axis of the drive shaft 204. This can be particularly useful when bending or cutting an implant that is at least partially implanted in a patient, as it provides flexibility for instrument positioning to avoid patient anatomy or other obstacles.

FIGS. 20-24 illustrate an exemplary embodiment of an instrument 300 which can be used, for example, to cut an implant.

The instrument 300 generally includes an adapter 302, a drive shaft 304, a cutting wheel 306, and a cutting plate 308. In use, an implant can be inserted through the cutting wheel 306 and the cutting plate 308. The drive shaft 304 can be rotated to turn the cutting wheel 306 with respect to the cutting plate 308, thereby applying a shear force to the implant to cut or sever the implant.

The adapter 302 can include a housing 310 in which the drive shaft 304 is rotatably disposed and to which the cutting wheel 306 and cutting plate 308 are mounted. A retention ring or washer 312 can be mounted in corresponding grooves formed in the drive shaft 304 and the interior of the adapter housing 310 to maintain the drive shaft at a fixed longitudinal position with respect to the housing. A proximal end of the adapter 302 can include a mating feature for coupling the adapter to a driver tool (e.g., a manual, electric, hydraulic, or pneumatic drill or driver tool). An exemplary battery-powered driver tool is described below and shown in FIG. 25. The illustrated adapter 302 is configured for use with a driver tool that includes a rotating component sized to fit within a proximal cylindrical opening of the adapter housing 310 to engage a drive feature 314 formed at the proximal end of the drive shaft 304. The adapter housing 310 is non-rotatably coupled to a non-rotating component of the driver tool. Accordingly, when the driver tool is actuated, the drive shaft 304 rotates relative to a handle portion of the driver tool while the adapter housing 310 remains stationary with respect to the handle portion of the driver tool. The adapter housing 310 can include one or more pins or other anti-rotation features to prevent the adapter housing from rotating relative to the driver tool.

The drive shaft 304 can be an elongate cylindrical rod having proximal and distal ends and configured to rotate about a rotation axis R1. The drive shaft 304 can include a threaded portion or worm screw 316. The worm screw 316 can be formed integrally with the drive shaft 304. In the illustrated embodiment, however, the worm screw 316 is formed as a separate sleeve component in which the drive shaft 304 is received. The longitudinal position of the worm screw 316 with respect to the drive shaft 304 can fixed by first and second retaining caps 318. At least one of the retaining caps 318 can be formed integrally with the drive shaft 304. The rotational position of the worm screw 316 with respect to the drive shaft 304 can be fixed by an elongated tab or key 320 that sits within corresponding grooves formed in the exterior surface of the drive shaft and the interior surface of the worm screw.

The drive shaft 304 can be mounted in proximal and distal bearing assemblies 322 disposed within the adapter housing 310 to facilitate rotation of the drive shaft relative to the adapter housing. As shown, the first and second retaining caps 318 can include reduced-diameter shaft portions 324 over which the bearing assemblies 322 are mounted. While any of a variety of bearing assemblies can be used, the illustrated bearing assemblies 322 are race bearings that include an outer race 326, an inner race 328, and at least one ball bearing 330 disposed within respective annular tracks formed in the outer and inner races. The race bearings can also include proximal and distal retaining washers 332. The outer races 326 can be press fit or otherwise coupled to the adapter housing 310 and the inner races 328 can be press fit or otherwise coupled to the retaining caps 318 such that rotation of the drive shaft 304 relative to the adapter housing 310 causes the inner race to rotate relative to the outer race, with the ball bearing 330 reducing the friction associated with said rotation.

The cutting wheel 306 can have a plurality of teeth formed on an exterior circumferential surface thereof configured to engage the threaded portion 316 of the drive shaft 304 such that rotation of the drive shaft 304 about the axis R1 causes the cutting wheel to rotate about its central axis R2. As shown, the axis R2 can extend perpendicular to a plane in which the axis R1 lies. In some embodiments, the cutting wheel 306 and the drive shaft 304 can form a worm drive, in which the teeth of the cutting wheel 306 form the worm wheel and the threaded portion 316 of the drive shaft forms the worm screw. The size, number, and spacing of the teeth, as well as the size of the cutting wheel 306, can be selected to increase or decrease the torque applied to the cutting wheel or the rotating speed of the cutting wheel.

The cutting wheel 306 can include an axle 334 that can be rotatably mounted in an opening 336 formed in the adapter housing 310. As shown, the toothed portion of the cutting wheel 306 can be rotationally fixed relative to the axle 334 by an elongated tab or key 338 that sits within corresponding grooves formed in the exterior surface of the axle and the interior surface of the toothed portion. Alternatively, the toothed portion can be formed integrally with the axle. A circlip or other retaining member 340 can be seated within a groove formed in the axle 334 to retain the axle within the opening 336 formed in the adapter housing 310. The axle 334 can include at least one hole or through-bore 342 in which an implant can be received.

The cutting plate 308 can be formed integrally with the adapter housing 310 or can be coupled thereto as shown. The illustrated cutting plate 308 includes a disc-shaped plate having at least one opening 344 formed therein in which an implant can be received. Any of a variety of techniques can be used to attach the cutting plate 308 to the adapter housing 310. For example, the cutting plate 308 can include one or more holes 346 in which a screw or bolt can be received to secure the cutting plate to the adapter housing 310. The cutting plate 308 can be rotationally fixed relative to the adapter housing 310.

In use, the cutting wheel 306 can be positioned such that at least one of the openings 342 formed therein for receiving an implant is aligned with an opening 344 formed in the cutting plate 308. An implant (e.g., a spinal rod) that is to be cut can be inserted through the opening 342 formed in the cutting wheel 306 and through the opening 344 formed in the cutting plate 308. A user can then actuate a driver tool to which the instrument 300 is coupled to rotate the drive shaft 304 and the worm screw 316. Rotation of the worm screw 316 causes the cutting wheel 306 (via the worm gear formed thereon) to rotate relative to the adapter housing 310 and relative to the cutting plate 308, which is rotationally fixed to the adapter housing. Accordingly, the sidewalls of the openings 342, 344 exert a shear force on the implant inserted therethrough, cutting or severing the implant. In some embodiments, the sidewalls of one or more of the openings 342, 344 can be tapered or ramped to provide sharpened portion(s) (e.g., at the cutting interface between the wheel 306 and the plate 308).

The illustrated instrument 300 includes three implant openings 342 in the cutting wheel 306 and one implant opening 344 in the cutting plate 308, though it will be appreciated that either component can include any number of implant openings. Inclusion of a plurality of implant openings can advantageously increase the number of rotational positions of the cutting wheel 306 at which at least one opening is aligned with an opening of the cutting plate 308.

Figure 24:
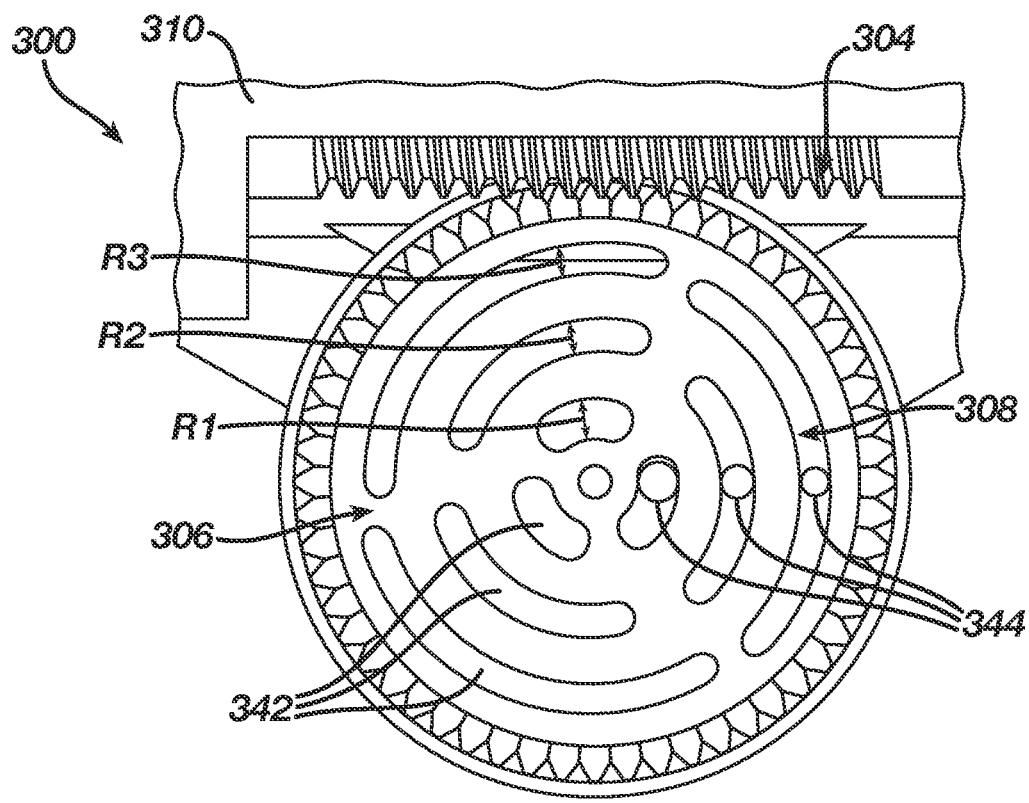
FIG. 24 is a lateral profile view of the instrument of FIG. 20 with an alternate cutting wheel.

In some embodiments, as shown in FIG. 24, the implant openings formed in either the cutting wheel 306 or the cutting plate 308 can be elongated to further increase the number of rotational positions of the cutting wheel at which at least one opening 342 is aligned with an opening 344 of the cutting plate. While bean-shaped openings 342 are shown, the openings can have any of a variety of other shapes (e.g., trapezoidal, ramped or blade-shaped, etc.). While only the cutting wheel openings 342 are elongated in the illustrated embodiment, the openings 344 in the cutting plate 308 can be elongated instead or in addition.

As also shown in FIG. 24, the cutting wheel 306 and/or the cutting plate 308 can include implant openings of various sizes to facilitate use of the instrument with implants having various sizes (e.g., spinal rods having different diameters). For example, the cutting wheel 306 can include a plurality of openings 342 arranged in concentric ring patterns. The openings 342 of each ring can have a radial dimension that differs from that of one or more (or all) of the other rings. In the embodiment of FIG. 24, the inner-most ring of openings 342 has a radial dimension R1, the middle ring of openings 342 has a radial dimension R2, and the outer-most ring of openings 342 has a radial dimension R3, where R1>R2>R3. In an exemplary embodiment, R1 can be about 6.35 mm, R2 can be about 5.5 mm, and R3 can be about 4.5 mm. Similarly, the cutting plate 308 can include openings 344 that vary in diameter in accordance with the ring of cutting wheel openings 342 with which they are aligned.

As noted above, the cutting plate 308 can be formed integrally with the adapter housing 310. In other words, the cutting plate 308 can be omitted and the adapter housing 310 itself can serve as the cutting plate.

Figure 25:
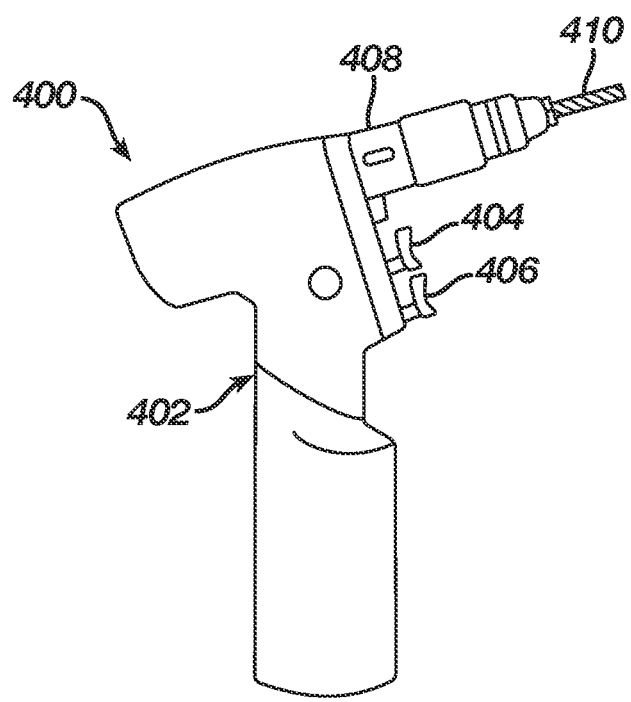
FIG. 25 is a profile view of an exemplary driver tool configured for use with the instruments described herein.

FIG. 25 illustrates an exemplary embodiment of a driver tool 400 that can be used with any of the instruments disclosed herein. The driver tool 400 generally includes a handle portion 402 with first and second actuation buttons 404, 406, a non-rotating mating portion 408 configured to mate the driver tool 400 with an adapter of an instrument (e.g., the instruments 100, 200, 300 described herein), and a rotating component 410 configured to mate with and rotate the drive shaft of an instrument (e.g., the instruments 100, 200, 300 described herein). The rotating component 410 can be driven by a motor and a power source (e.g., a battery) disposed in the driver tool 400. In some embodiments, one of the actuation buttons 404, 406 can be depressed to rotate the rotating component 410 clockwise and the other of the actuation buttons 404, 406 can be depressed to rotate the rotating component counterclockwise. Other exemplary driver tools include the Colibri II System (a compact and modular Li-Ion-battery-driven power tool) available from DePuy Synthes.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

As evident from the foregoing, in at least some embodiments, the instruments disclosed herein can provide one or more advantages as compared with other instruments:

The instruments 100, 200, 300 can provide quicker and more efficient bending and/or cutting of implants.

The instruments 100, 200, 300 can be small and portable which can allow them to be brought closer to the patient and surgical site to bend or cut an implant without leaving the patient or to bend or cut an implant that is at least partially implanted in the patient.

The instruments 100, 200, 300 can be driven by power tools and can require less input force, reducing surgeon fatigue and strength requirements.

The instruments 100, 200, 300 can allow for precise and repeatable bending of implants.

The instruments 100, 200, 300 can allow for bending of implants to a desired shape in fewer iterations, reducing the risk of lowered implant fatigue strength.

The instruments disclosed herein can be constructed from any of a variety of known materials. Exemplary materials include those which are suitable for use in surgical applications, including metals such as stainless steel, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of bending a rod or bone plate in spine or trauma surgery, it will be appreciated that the methods and devices disclosed herein can be used with any human or animal implant, in any of a variety of surgeries performed on humans or animals, and/or in fields unrelated to implants or surgery.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A method of bending or cutting an implant using an instrument, comprising:
    positioning an implant between first and second portions of a bending or cutting template of the instrument; and
    rotating a drive shaft of the instrument to urge the first and second portions of the template toward one another along a longitudinal axis of the drive shaft to bend or cut the implant,
    wherein rotating the drive shaft comprises selecting between rotating the drive shaft in a first direction to bend the implant proximally and rotating the drive shaft in a second, opposite direction to bend the implant distally.

2. The method of claim 1, wherein the first portion of the template is coupled to a body of the instrument and the second portion of the template is coupled to a pusher of the instrument.

3. A method of bending or cutting an implant using an instrument, comprising:
    positioning an implant between first and second portions of a bending or cutting template of the instrument; and
    rotating a drive shaft of the instrument to urge the first and second portions of the template toward one another along a longitudinal axis of the drive shaft to bend or cut the implant;
    wherein rotating the drive shaft actuates a scissor linkage to provide a mechanical advantage in urging the pusher towards the body.

4. A method of bending or cutting an implant using an instrument, comprising:
    positioning an implant between first and second portions of a bending or cutting template of the instrument; and rotating a drive shaft of the instrument to urge the first and second portions of the template toward one another along a longitudinal axis of the drive shaft to bend or cut the implant;
wherein rotating the drive shaft pulls first and second arms of the instrument inwards towards the drive shaft.

5. A method of bending or cutting an implant using an instrument, comprising:
positioning an implant between first and second portions of a bending or cutting template of the instrument; and
rotating a drive shaft of the instrument to urge the first and second portions of the template toward one another along a longitudinal axis of the drive shaft to bend or cut the implant;
wherein the implant is at least partially implanted in a patient during said positioning and said rotating.

6. A method of bending or cutting an implant using an instrument, comprising:
positioning an implant between first and second portions of a bending or cutting template of the instrument;
rotating a drive shaft of the instrument to urge the first and second portions of the template toward one another along a longitudinal axis of the drive shaft to bend or cut the implant; and
adjusting a distance between components of the first portion of the template to adjust an angle of a bend formed in the implant.

7. A method of bending or cutting an implant using an instrument, comprising: inserting an implant within a body of an instrument, the instrument having a pusher and a bending or cutting template having the implant disposed therebetween, and a drive shaft that extends through a bore formed in the pusher;
positioning the implant between a first portion and a second portion of the bending or cutting template, the first portion and the second portion having one or more rollers configured to engage opposing surfaces of the implant;
actuating the instrument to exert a bending or cutting force onto the implant; and
coupling a driver tool to a proximal end of the drive shaft to rotate the drive shaft with respect to the pusher and the cutting template;
wherein rotation of the drive shaft in a first direction pulls the pusher towards the body to bend the implant proximally and rotation of the drive shaft in a second, opposite direction pushes the pusher away from the body to bend the implant distally.

8. The method of claim 7, wherein actuating the instrument further comprises rotating the drive shaft to translate the pusher relative to the body to exert the bending or cutting force onto the implant.

9. The method of claim 7, wherein the pusher moves towards and away from the body along a longitudinal axis of the drive shaft.

10. The method of claim 7, wherein a degree of the bend formed in the implant is controlled by a number of rotations of the drive shaft.

11. The method of claim 7, further comprising replacing one or more rollers of the template with a roller having a specific radius of curvature to adjust a bend formed in the implant.

12. The method of claim 7, further comprising:
repositioning the implant within the body of the instrument such that the template contacts an unbent portion of the implant, and
actuating the instrument to exert a bending or cutting force onto the implant.

13. The method of claim 7, further comprising adjusting a position of the pusher prior to inserting the implant into the instrument to accommodate an implant having a previously-formed bend therein.

14. The method of claim 7, wherein the implant is partially implanted within a body of a patient.

15. The method of claim 7, wherein the implant is one or more of a spinal rod or a bone plate.

16. The method of claim 7, wherein the pusher is prevented from rotating with respect to the body by the implant during actuation of the instrument.

17. The method of claim 7, wherein positioning the implant further comprises disposing the implant in one or more recesses formed in the template to create an interference fit that prevents rotation of the pusher with respect to the body.

18. A method of bending or cutting an implant using an instrument, comprising:
inserting an implant within a body of an instrument, the instrument having a pusher and a bending or cutting template having the implant disposed therebetween, and a drive shaft that extends through a bore formed in the pusher;
positioning the implant between a first portion and a second portion of the bending or cutting template, the first portion and the second portion having one or more rollers configured to engage opposing surfaces of the implant;
actuating the instrument to exert a bending or cutting force onto the implant; and
replacing one or more rollers of the template with a roller having a specific radius of curvature to adjust a bend formed in the implant.

19. A method of bending or cutting an implant using an instrument, comprising:
inserting an implant within a body of an instrument, the instrument having a pusher and a bending or cutting template having the implant disposed therebetween, and a drive shaft that extends through a bore formed in the pusher;
positioning the implant between a first portion and a second portion of the bending or cutting template, the first portion and the second portion having one or more rollers configured to engage opposing surfaces of the implant;
actuating the instrument to exert a bending or cutting force onto the implant; and
adjusting a position of the pusher prior to inserting the implant into the instrument to accommodate an implant having a previously-formed bend therein.

20. A method of bending or cutting an implant using an instrument, comprising:
inserting an implant within a body of an instrument, the instrument having a pusher and a bending or cutting template having the implant disposed therebetween, and a drive shaft that extends through a bore formed in the pusher;
positioning the implant between a first portion and a second portion of the bending or cutting template, the first portion and the second portion having one or more rollers configured to engage opposing surfaces of the implant; and
actuating the instrument to exert a bending or cutting force onto the implant;

wherein the implant is partially implanted within a body of a patient.

* * * * *